(12) United States Patent
Zhang et al.

(10) Patent No.: US 12,312,333 B2
(45) Date of Patent: May 27, 2025

(54) SK CHANNEL POSITIVE ALLOSTERIC MODULATORS

(71) Applicants: Chapman University, Orange, CA (US); The Board of Regents of The University of Texas System, Austin, TX (US); Northeastern University, Boston, MA (US)

(72) Inventors: Miao Zhang, Orange, CA (US); Keykavous Parang, Orange, CA (US); Naglaa Ibrahim, Orange, CA (US); Young Woo Nam, Orange, CA (US); Ilya Bezprozvanny, Austin, TX (US); Meng Cui, Boston, MA (US)

(73) Assignees: Chapman University, Orange, CA (US); The Board of Regents of University of Texas System, Austin, TX (US); Northeastern University, Boston, MA (US)

( * ) Notice: Subject to any disclaimer, the term of this patent is extended or adjusted under 35 U.S.C. 154(b) by 0 days.

(21) Appl. No.: 17/956,553

(22) Filed: Sep. 29, 2022

(65) Prior Publication Data

US 2023/0159500 A1    May 25, 2023

Related U.S. Application Data

(60) Provisional application No. 63/250,476, filed on Sep. 30, 2021.

(51) Int. Cl.
| | | |
|---|---|---|
| C07D 403/04 | (2006.01) | |
| C07D 403/14 | (2006.01) | |
| C07D 413/04 | (2006.01) | |

(52) U.S. Cl.
CPC ......... *C07D 403/04* (2013.01); *C07D 403/14* (2013.01); *C07D 413/04* (2013.01)

(58) Field of Classification Search
None
See application file for complete search history.

(56) References Cited

U.S. PATENT DOCUMENTS

2017/0355708 A1 * 12/2017 Jefson ................ C07D 491/107

FOREIGN PATENT DOCUMENTS

WO    WO 2006/100212 A1 * 9/2006 ........... C07D 403/04

OTHER PUBLICATIONS

Wan-Yin Fang et al , synthetic approaches and pharmaceutical applications of chloro-containing molecules for drug discovery: A critical review European Journal of Medicinal Chemistry, vol. 173, Jul. 1, 2019, pp. 117-153 (Year: 2019).*

Poonam Shah et al., The role of fluorine in Medicinal Chemistry, Journal of Enzyme inhibition and Medicinal chemistry vol. 22, 527-540, 2007 (Year: 2007).*

Life Chemicals, Inc., "RN 1019106-73-0", Chemical Library, 2008, 1 page (Year: 2008).*

El-Sayed N.S., et al. "Structure-Activity Relationship Study of Subtype-Selective Positive Modulators of KCa2 Channels" J. Med. Chem. 65(1):303-322, 2022.

Womack, M. D. and Khodakhah, K., Somatic and Dendritic Small-Conductance Calcium-Activated Potassium Channels Regulate the Output of Cerebellar Purkinje Neurons.} J. Neurosci. 23(7):2600-2607, 2003.

(Continued)

*Primary Examiner* — Brenda L Coleman
*Assistant Examiner* — Madeline E Braun
(74) *Attorney, Agent, or Firm* — K&L Gates LLP; Louis C. Cullman; Giorgios N. Kefallinos

(57) ABSTRACT

A compound according to Formula (I) or a pharmaceutically acceptable salt thereof:

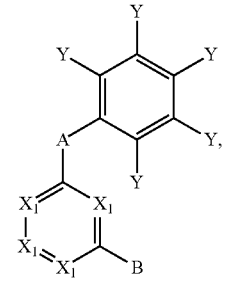

Formula (I)

is provided. $X_1$ is N or C—Y; Y is H, halogen, $NH_2$, OH, SH, alkyl, aryl, alkoxy, or aryloxy; A is O, NH, S, Se, or $CH_2$, B is

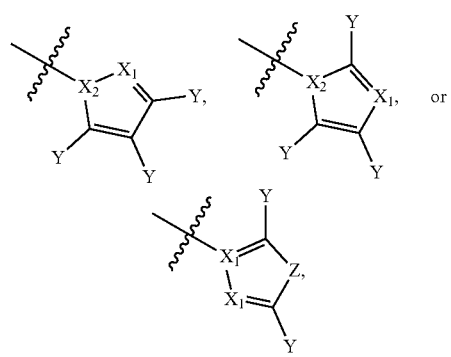

$X_2$ is N or CH; and Z is NH, $CH_2$, S, O, or Se.

9 Claims, 10 Drawing Sheets

(56) References Cited

OTHER PUBLICATIONS

Geschwind, D. H. et al. "The prevalence and wide clinical spectrum of the spinocerebellar ataxia type 2 trinucleotide repeat in patients with autosomal dominant cerebellar ataxia." Am J Hum Genet 60(4):842-50. 1997.

Brown, B. M. et al. "Pharmacology of Small- and Intermediate-Conductance Calcium-Activated Potassium Channels". Annu Rev Pharmacol Toxicol 60:219-240, 2020.

Cingolani, L. A. et al. "Developmental regulation of small-conductance Ca2+-activated K+ channel expression and function in rat Purkinje neurons." J Neurosci 22(11);4456-67, 2002.

Hosy, E. et al. "SK2 channel expression and function in cerebellar Purkinje cells." J Physiol 589(Pt 14):3433-40, 2011.

Hougaard, C. et al. "Selective positive modulation of the SK3 and SK2 subtypes of small conductance Ca2+-activated K+ channels." British journal of pharmacology, 151(5):655-65, 2007.

Lee, C. H. and MacKinnon, R. "Activation mechanism of a human SK-calmodulin channel complex elucidated by cryo-EM structures." Science 360(6388):508-513, 2018.

Cho, L. T. et al. "An Intracellular Allosteric Modulator Binding Pocket in SK2 Ion Channels Is Shared by Multiple Chemotypes." Structure 26(4):533-544 e3, 2018.

Nam, Y. W. et al. "Hydrophobic interactions between the HA helix and S4-S5 linker modulate apparent Ca(2+) sensitivity of SK2 channels." Acta Physiol (Oxford) e13552, 2020.

Nam, Y.-W. et al. "Subtype-selective positive modulation of KCa 2 channels depends on the HA/HB helices." British journal of pharmacology 179:460-72, 2021.

Kasumu, A. W. et al. "Selective positive modulator of calcium-activated potassium channels exerts beneficial effects in a mouse model of spinocerebellar ataxia type 2." Chem Biol 19(10):1340-53. 2012.

Kasumu, A. W. et al. "Chronic suppression of inositol 1,4,5-triphosphate receptor-mediated calcium signaling in cerebellar purkinje cells alleviates pathological phenotype in spinocerebellar ataxia 2 mice." J Neurosci 32 (37), 12786-96, 2012.

Egorova, P. A. et al. "Ataxic Symptoms in Huntington's Disease Transgenic Mouse Model Are Alleviated by Chlorzoxazone." Front Neurosci 14:279, 2020.

Egorova, P. A. and Bezprozvanny, I. B., "Molecular Mechanisms and Therapeutics for Spinocerebellar Ataxia Type 2." Neurotherapeutics 16(4):1050-1073, 2019.

\* cited by examiner

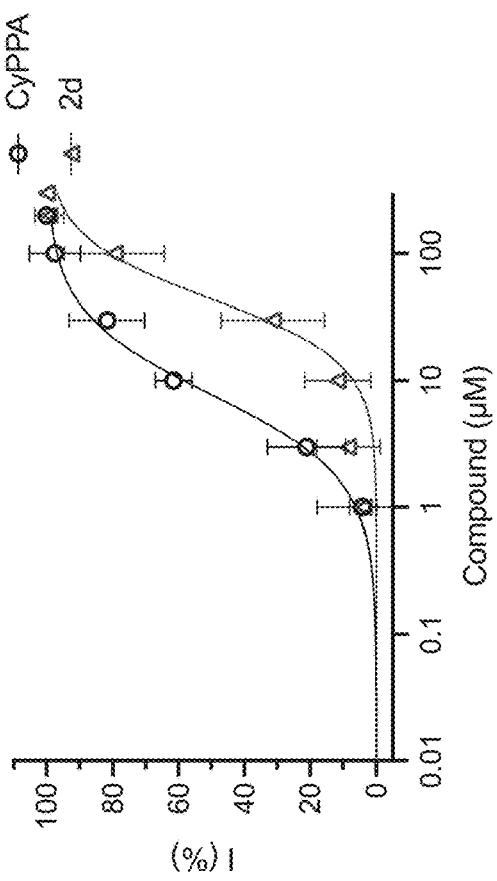
FIG. 1A
FIG. 1B
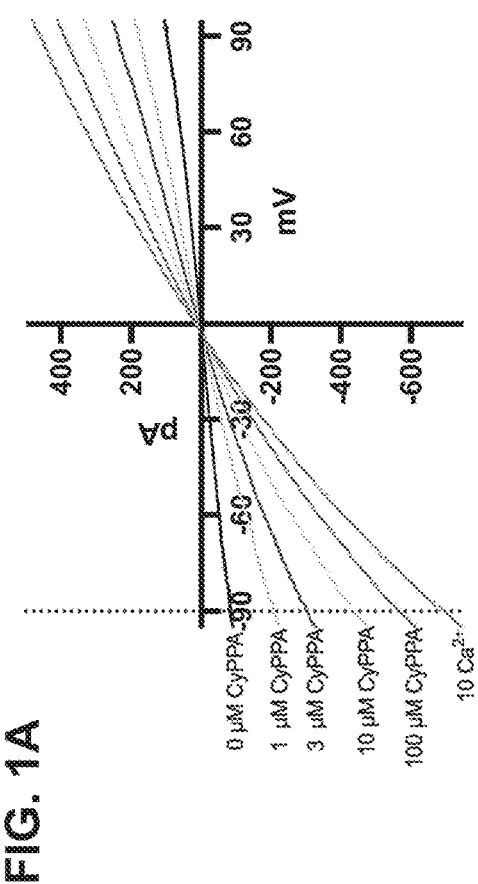
FIG. 1C
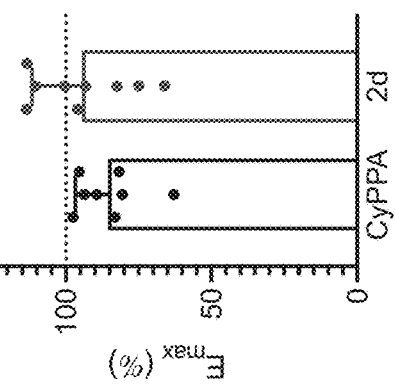
FIG. 1D
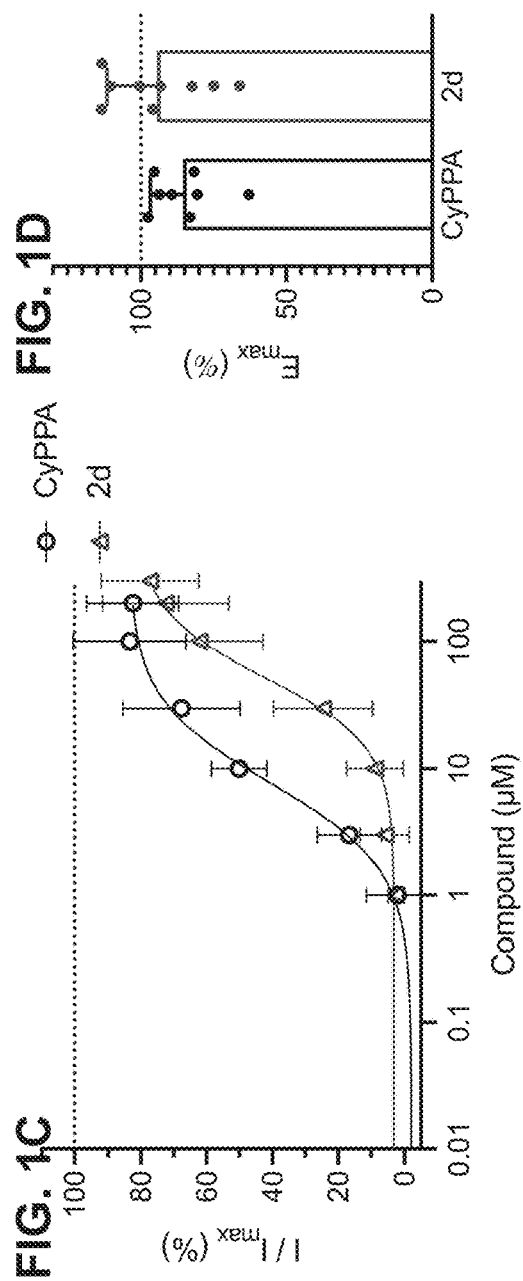

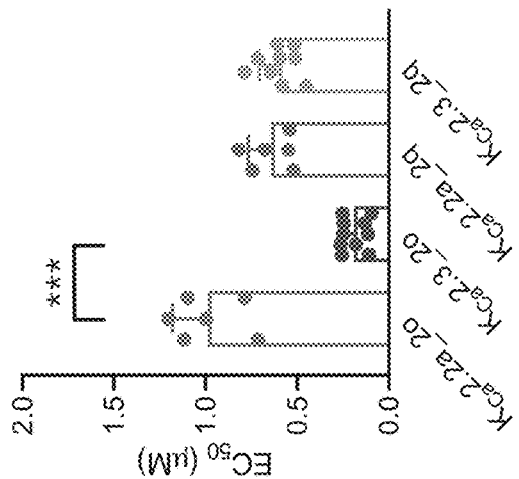
FIG. 7B
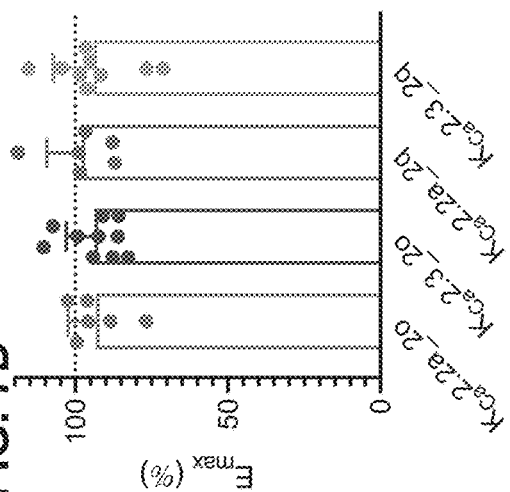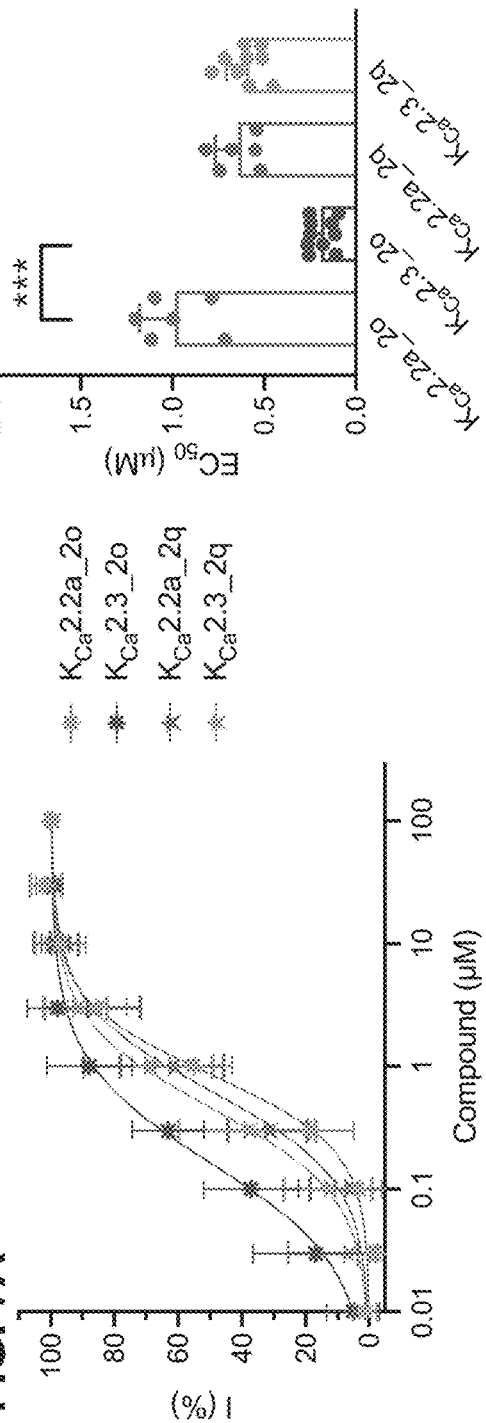
FIG. 7A
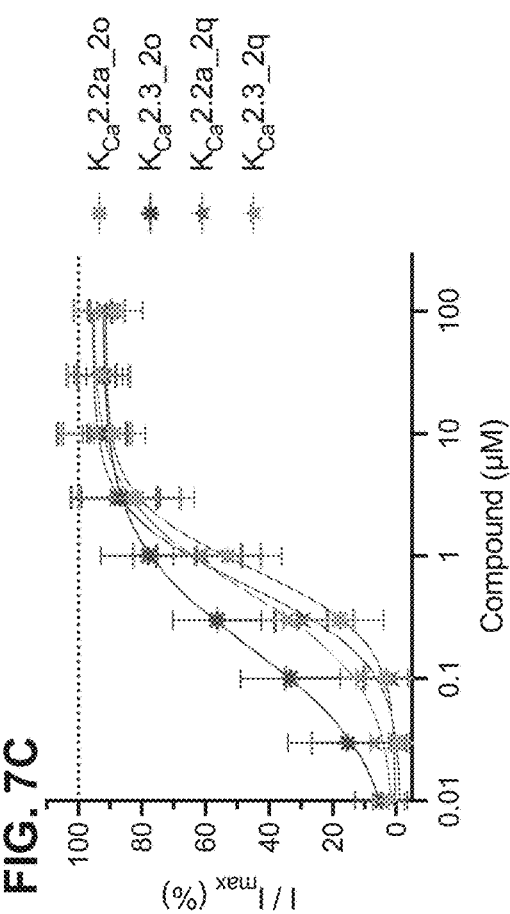
FIG. 7C
FIG. 7D

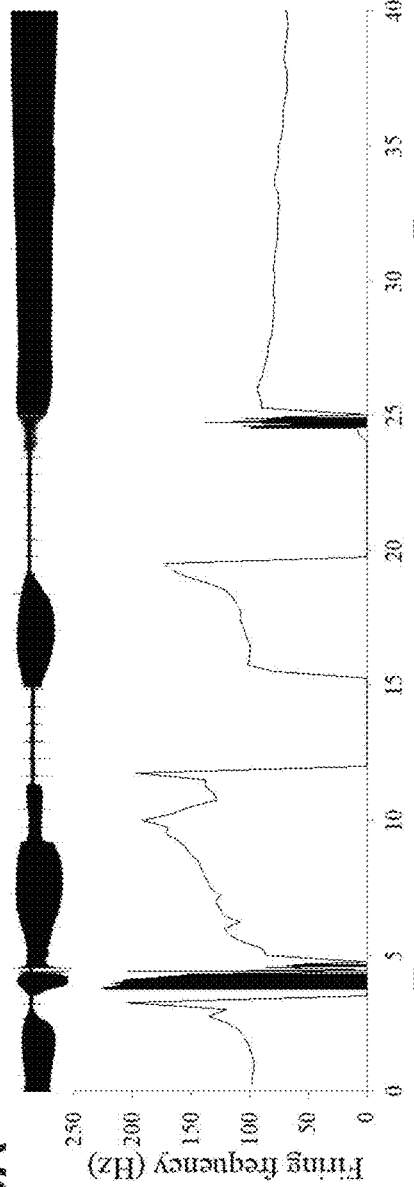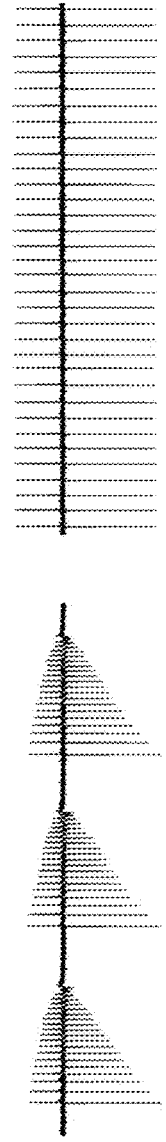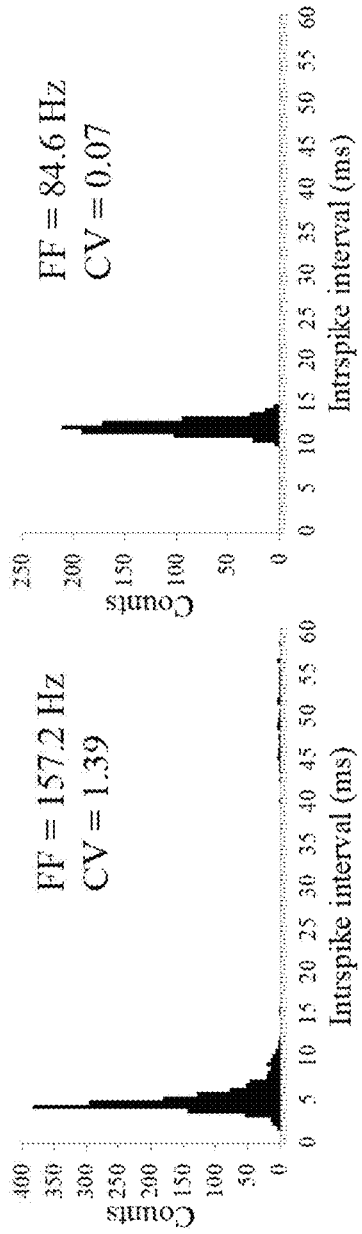
FIG. 9A
FIG. 9B
FIG. 9C

SK CHANNEL POSITIVE ALLOSTERIC MODULATORS

CROSS REFERENCE TO RELATED APPLICATIONS

This application claims the benefit of U.S. Provisional patent application 63/250,476 filed Sep. 30, 2021, the entire contents of which is incorporated by reference herein.

STATEMENT REGARDING FEDERALLY SPONSORED RESEARCH OR DEVELOPMENT

This invention was made with government support under Grant Nos. 4R33NS101182 and R01NS056224 awarded by the National Institutes of Health. The government has certain rights in the invention.

FIELD

The present disclosure relates to compounds that are SK channel positive allosteric modulators, methods of preparing these compounds, and the use of these compounds in potentiating SK channels.

BACKGROUND

Small-conductance $Ca^{2+}$-activated $K^+$ ($K_{Ca}2$ or SK) channels have emerged as one of the principal ion channels involved in the pacemaking of cerebellar Purkinje cells (PCs). Cerebellar PCs are the primary locus of the pathology of spinocerebellar ataxia (SCA). There are four mammalian genes identified in the KCNN family, including KCNN1 encoding $K_{Ca}2.1$ (SK1), KCNN2 encoding $K_{Ca}2.2$ (SK2), KCNN3 encoding $K_{Ca}2.3$ (SK3), and KCNN4 encoding $K_{Ca}3.1$ (SK4, IK) channels, respectively. Among the $K_{Ca}2.x/K_{Ca}3.1$ channel subtypes, $K_{Ca}2.2$ is the predominant subtype that is expressed in the cerebellum. Loss-of-function mutations that diminish $K_{Ca}2.2$ channel activity have been linked with tremor and ataxia symptoms in rodents and humans.

For decades, tremendous efforts have been devoted to the development of subtype-selective positive modulators of $K_{Ca}2$ channels. The prototype subtype-selective positive modulator CyPPA has been previously reported to potentiate the $K_{Ca}2.2$ and $K_{Ca}2.3$, but not the $K_{Ca}2.1$ and $K_{Ca}3.1$ channel subtypes. The low potency of CyPPA in the micromolar range makes it unfit for clinical use. Recently, the structure of human $K_{Ca}3.1$ channels has been determined by cryogenic-electron microscopy (cryo-EM). These full-length structures, including the transmembrane domains are better tools for structure-aided drug discovery than the crystal structure of the cytoplasmic domain.

Small-conductance calcium-activated potassium channels (SK channels) can be operationally defined as those having single-channel conductance of less than 20 pS. These channels are found in a wide range of excitable and non-excitable cells. In nerve and muscle, the ionic currents that flow through these channels are responsible for maintaining the slow after-hyperpolarizing potential (AHP) that follows bursts of action potentials. The small- and intermediate-conductance Ca2+-activated K+(SK/IK) channels play an important role in the regulation of neurons in the central nervous system. In animal models, SK/IK channel positive modulators have been shown to be effective in reducing the symptoms of neurological diseases such as ataxia. Ataxia is a lethal neurological rare disease characterized by lack of balance and incoordination of muscle movements, often as a result of cerebellar or spinocerebellar neurodegeneration. SK/IK channel modulators have been developed over the past few decades. Currently available modulators are often weak in potency. Lack of knowledge about the binding site for the compounds is a primary reason hindering the development of more potent and effective therapeutics targeting SK channels.

SUMMARY

A homology model of the $K_{Ca}2.2a$ channel was generated using the $K_{Ca}3.1$ channel cryo-EM structure in the presence of $Ca^{2+}$ (PDB: 6cnn). The $K_{Ca}2$ channels can form homo-tetramers in a complex with four of the $Ca^{2+}$-binding protein calmodulin (CaM). In the presence of $Ca^{2+}$, the C-lobe of CaM is associated with the channel alpha subunits at the HA/HB helices formed by the CaM binding domain (CaM-BD), while the N-lobe of CaM contacts the $S_{45}A$ helix of a neighboring subunit's S4-S5 linker. With combined computational, site-directed mutagenesis and electrophysiology approaches, a pocket for CyPPA was identified between the HA/HB helices and the C-lobe of CaM.

After elucidating the CyPPA-channel interactions from the perspective of the drug target, the synthesis and evaluation of a new series of CyPPA analogs are discussed. Considering the largely hydrophobic nature of the pocket between CaM C-lobe and the HA/HB helices, the impact of replacing the cyclohexane moiety in CyPPA with different 4-substituted cyclohexyl rings, tyrosine analogs, mono and di-halogen substituted phenyl rings was evaluated. Changing the position of attached pyrazole and replacing it with an oxazolyl or imidazolyl ring, as well as replacing the pyrimidine ring with pyridazine ring were also studied. A number of newly developed compounds demonstrated the ability to potentiate activity of $K_{Ca}2.2a$ channels while retaining the $K_{Ca}2.2a/K_{Ca}2.3$ subtype selectivity, and to normalize firing of cerebellar PCs in the model of spinocerebellar ataxia type 2 (SCA2).

A series of modified N-cyclohexyl-2-(3,5-dimethyl-1H-pyrazol-1-yl)-6-methylpyrimidin-4-amine (CyPPA) analogs were synthesized by replacing the cyclohexane moiety with different 4-substituted cyclohexane rings, tyrosine analogs, or mono and dihalophenyl rings, and were subsequently studied for their potentiation of $K_{Ca}2$ channel activity. Among the N-benzene-N-[2-(3,5-dimethyl-pyrazol-1-yl)-6-methyl-4-pyrimidinamine derivatives, halogen decoration at positions 2 and 5 or 3 and 4 positions of benzene-substituted 4-pyrimidineamine in compounds 2q and 2o conferred ~10- or ~7-fold higher potency on potentiating $K_{Ca}2.2a$ channels, respectively, compared to the parent template CyPPA. Both compounds retained the $K_{Ca}2.2a/K_{Ca}2.3$ subtype selectivity. Compounds 2o and 2q were tested in electrophysiological model of spinocerebellar ataxia type 2 (SCA2). Both compounds were able to normalize abnormal firing of Purkinje cells in cerebellar slices from SCA2 mouse model, demonstrating the potential therapeutic potential of these compounds for treating symptoms of ataxia.

Disclosed herein are compounds according to Formula (I) or pharmaceutically acceptable salts thereof:

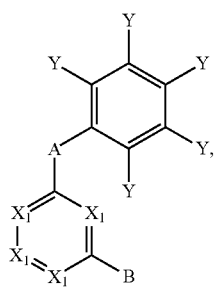

Formula (I)

$X_1$ is N or C—Y; Y is H, halogen, $NH_2$, OH, SH, alkyl, aryl, alkoxy, or aryloxy; A is O, NH, S, Se, or $CH_2$, B is

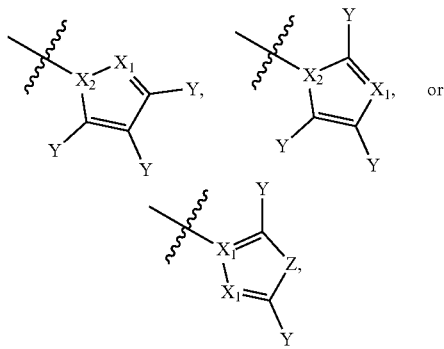

$X_1$ or $X_2$ is N or CH, and Z is NH, $CH_2$, S, O, or Se.

Also disclosed herein are methods of potentiating SK channels in subjects in need thereof comprising administering therapeutically effective amounts of the foregoing compounds or the pharmaceutically acceptable salts thereof, or pharmaceutical compositions including the foregoing compounds or the pharmaceutically acceptable salts thereof.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, as will occur to one having ordinary skill in the art and having the benefit of this disclosure.

FIG. 1A-D. Optimization of the cyclohexane moiety. (FIG. 1A) Representative current traces of concentration-dependent potentiation by CyPPA of $K_{Ca}2.2a$ channels. (FIG. 1B) Concentration-dependent potentiation by 2d and CyPPA of $K_{Ca}2.2a$ channels. (FIG. 1C) Responses to 2d and CyPPA of $K_{Ca}2.2a$ channels were normalized to the maximal currents induced by 10 μM $Ca^{2+}$. (FIG. 1D) $E_{max}$ to 2d and CyPPA of $K_{Ca}2.2a$ channels.

(FIG. 2A) Potentiation by compounds with decorated phenyl moiety and CyPPA of $K_{Ca}2.2a$ channels. (FIG. 2B) $EC_{50}$ values for potentiation by compounds with decorated phenyl moiety and CyPPA. (FIG. 2C) Responses to compounds of $K_{Ca}2.2a$ channels. The responses were normalized to the maximal currents induced by 10 μM $Ca^{2+}$. (FIG. 2D) $E_{max}$ to compounds. * P<0.05, *** P<0.001. No asterisk means no statistical significance compared with CyPPA.

(FIG. 3A) Potentiation by compounds with modified pyrimidine moiety and CyPPA of $K_{Ca}2.2a$ channels. (FIG. 3B) $EC_{50}$ values for potentiation by compounds with modified pyrimidine moiety and CyPPA. (FIG. 3C) Responses to compounds of $K_{Ca}2.2a$ channels. The responses were normalized to the maximal currents induced by 10 μM $Ca^{2+}$. (FIG. 3D) $E_{max}$ to compounds. *** P<0.001. No asterisk means no statistical significance.

(FIG. 4A) Potentiation by compounds with modified pyrazole moiety and CyPPA of $K_{Ca}2.2a$ channels. (FIG. 4B) $EC_{50}$ values for potentiation by compounds with modified pyrazole moiety and CyPPA. (FIG. 4C) Responses to compounds of $K_{Ca}2.2a$ channels. The responses were normalized to the maximal currents induced by 10 μM $Ca^{2+}$. (FIG. 4D) $E_{max}$ to compounds. * P<0.05, *** P<0.001. No asterisk means no statistical significance compared with its respective template.

(FIG. 5A) Lack of response to 2o of $K_{Ca}2.1$ channels. (FIG. 5B) Lack of response to 2q of $K_{Ca}2.1$ channels. (FIG. 5C) Responses to 2o and 2q of $K_{Ca}2.2a$ and $K_{Ca}2.1$ channels. The responses were normalized to the maximal currents induced by 10 μM $Ca^{2+}$. (FIG. 5D) $E_{max}$ to 2o and 2q of $K_{Ca}2.2a$ and $K_{Ca}2.1$ channels. *** P<0.001.

(FIG. 6A) Responses to 2o and 2q of $K_{Ca}2.2a$ and $K_{Ca}3.1$ channels. The responses were normalized to the maximal currents induced by 10 μM $Ca^{2+}$. (FIG. 6B) $E_{max}$ to 2o and 2q of $K_{Ca}2.2a$ and $K_{Ca}3.1$ channels. *** P<0.001.

FIG. 7A-D. Activity on $K_{Ca}2.3$ channels. (FIG. 7A) Potentiation by 2o and 2q of $K_{Ca}2.3$ channels compared to $K_{Ca}2.2a$ channels. (FIG. 7B) $EC_{50}$ values for potentiation by 2o and 2q of $K_{Ca}2.3$ channels compared to $K_{Ca}2.2a$ channels. (FIG. 7C) Responses to 2o and 2q of $K_{Ca}2.3$ channels compared to $K_{Ca}2.2a$ channels. The responses were normalized to the maximal currents induced by 10 μM $Ca^{2+}$. (FIG. 7D) $E_{max}$ to 2o and 2q of $K_{Ca}2.3$ channels compared to $K_{Ca}2.2a$ channels. *** P<0.001. No asterisk means no statistical significance compared with $K_{Ca}2.2a$ channel subtype.

(FIG. 8A) Continuous 40-min recording of PC activity. The time of 50 μM CHZ application is indicated by a horizontal bar above the recording. A plot of the running average of firing frequency is shown below the recording. (FIG. 8B) 390-ms fragments of PC activity recordings before the exposure to CHZ and 9 min after the exposure are shown on the expanded timescale. (FIG. 8C) The distributions of interspike intervals (ISI) before (left) and after (right) the exposure to CHZ were calculated from 10-s fragments of the recording shown in (FIG. 8A). Average firing frequency (FF) for the analyzed fragment before CHZ application was 141.6 Hz, and the CV of ISI in the analyzed fragment was 1.09. Average FF for the analyzed fragment after CHZ exposure was 67.3 Hz, and the CV of ISI was 0.05.

FIG. 9A-C. Subtype-selective $K_{Ca}2.2/K_{Ca}2.3$ channel positive allosteric modulator 2o converts bursting patterns into tonic activity of PC in acute cerebellar slices from 8-mo-old SCA2-58Q mouse. (FIG. 9A) Continuous 40-min recording of PC activity. The time of 10 μM 2o application is indicated by a horizontal bar above the recording. A plot of the running average of firing frequency is shown below the recording. (FIG. 9B) 390-ms fragments of PC activity recordings before the exposure to 2o and 12 min after the exposure are shown on the expanded timescale. (FIG. 9C) The distributions of interspike intervals (ISI) before (left) and after (right) the exposure to 2o were calculated from 10-s fragments of the recording shown in (FIG. 9A). Average firing frequency (FF) for the analyzed fragment before 2o application was 157.2 Hz, and the CV of ISI in the analyzed fragment was 1.39. Average FF for the analyzed fragment after 2o exposure was 84.6 Hz, and the CV of ISI was 0.07.

(FIG. 10A) Continuous 40-min recording of PC activity. The time of 10 uM 2q application is indicated by a horizontal bar above the recording. A plot of the running average of firing frequency is shown below the recording. (FIG. 10B) 390-ms fragments of PC activity recordings before the exposure to 2q and 7 min after the exposure are shown on the expanded timescale. (FIG. 10C) The distributions of interspike intervals (ISI) before (left) and after (right) the exposure to 2q were calculated from 10-s fragments of the recording shown in (FIG. 10A). Average firing frequency (FF) for the analyzed fragment before 2q application inside the bursts was 134.3 Hz, and the CV of ISI in the analyzed fragment was 1.83. Average FF for the analyzed fragment after 2q exposure was 55.9 Hz, and the CV of ISI was 0.21.

DETAILED DESCRIPTION

Figure 2A:
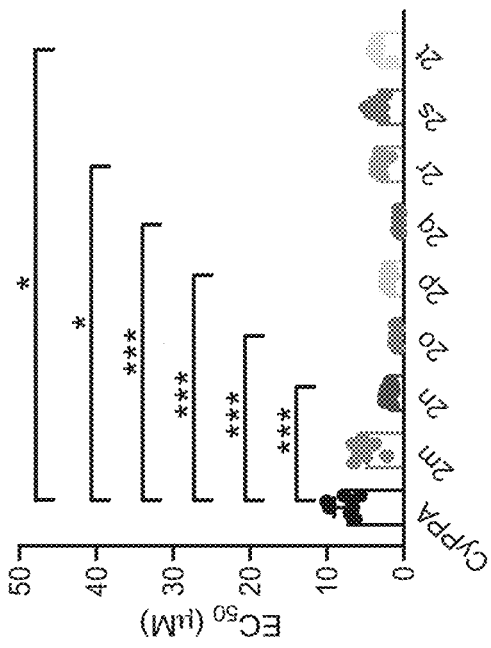
FIG. 2A-D. Optimization of the phenyl moiety.
Figure 2B:
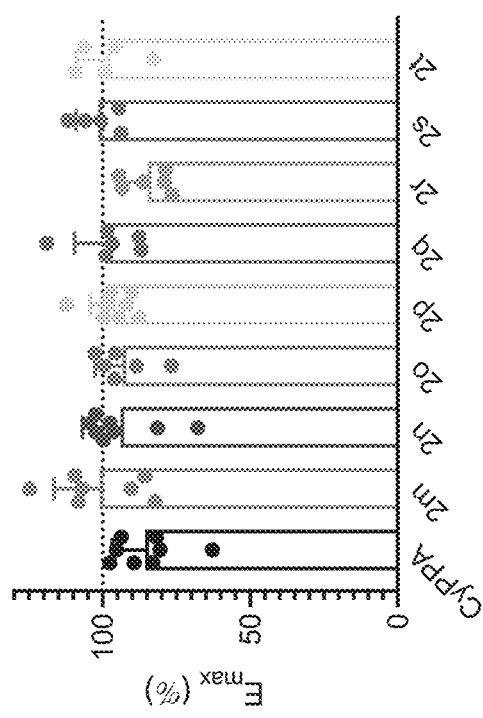

In neurons, activation of SK channels leads to reduced neuronal activity through their involvement in the medium after hyperpolarization (mAHP). Neuronal SK channels have been proposed as novel drug targets for spinocerebellar ataxias (SCAs) and other movement disorders. The most prevalent SCAs are genetic neurodegenerative disorder caused by polyglutamine (polyQ) repeat expansion in the affected genes, while rare types of SCAs can also be caused by non-repeat mutations. The cerebellar Purkinje cells are affected in many types of ataxia. The dysfunction of Purkinje cells, more specifically the loss of firing precision of Purkinje cells, is one of the primary mechanisms underlying the symptom of ataxia, especially SCAs. Disruptions of regular pacemaking activity of Purkinje cells have been identified in studies with mouse models of SCA3 and SCA2. Drugs that normalize the regular firing of Purkinje cells have been suggested as therapeutics for the symptom of ataxia patients. SK channels emerged as one of the principal ion channels involved in Purkinje cells pacemaking. Among the three SK channel subtypes, the SK2 channel subtype is the predominant subtype expressed in Purkinje cells. An isoleucine-to-asparagine (I289N) mutation was reported to cause diminished SK2 channel current and tremor in the tremor dominant Kyoto (Trdk) rats. A similar phenotype was observed in human caused by a glycine-to-glutamic acid (G371E) mutation of the KCNN2 gene. Indeed, loss-of-function mutations in the KCNN2 gene may lead to neurodevelopmental movement disorders including cerebellar ataxia. In mouse models of SCAs, positive SK channel modulators like chlorzoxazone, SKA31, and NS13001 exert beneficial effects through potentiating the SK2 channel subtype expressed in cerebellar Purkinje cells.

It is critical to identify subtype-selective SK channel modulators in order to minimize off target side effects. The prototypical subtype-selective positive modulator that enhances SK2 and SK3 channel activity but not the SK1 and IK channel activity is CyPPA. SK2/3 channel modulators with approximately 10 times higher potency that may become therapeutic agents for movement disorders including ataxias were identified.

Aspects of the present disclosure are directed to compounds according to Formula (I) or a pharmaceutically acceptable salt thereof:

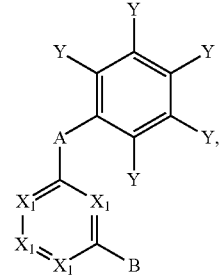

Formula (I)

wherein $X_1$ is N or C—Y,
Y is H, halogen, $NH_2$, OH, SH, alkyl, aryl, alkoxy, or aryloxy,
A is O, NH, S, Se, or $CH_2$,
B is

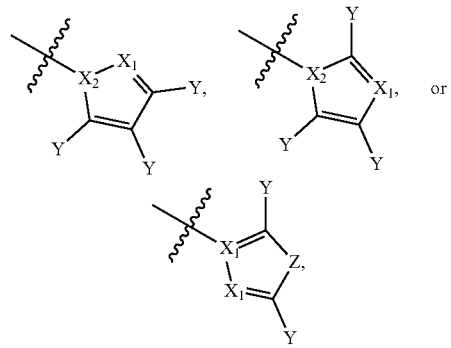

$X_1$ or $X_2$ is N or OH, and
Z is NH, $CH_2$, S, O, or Se.

In some embodiments, the compound is of Formula (Ia) or a pharmaceutically acceptable salt thereof:

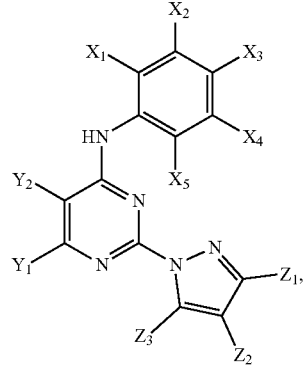

Formula (Ia)

wherein:
2k: $X_1$=$X_2$=$X_4$=$X_5$=H, $X_3$=SH, $Y_1$=$CH_3$, $Y_2$=H, $Z_1$=$CH_3$, $Z_2$=H, and $Z_3$=$CH_3$;

2l: $X_1=X_2=X_4=X_5=H$, $X_3=NO_2$, $Y_1=CH_3$, $Y_2=H$, $Z_1=CH_3$, $Z_2=H$, and $Z_3=CH_3$;

2m: $X_1=X_2=F$, $X_3=X_4=X_5=H$, $Y_1=CH_3$, $Y_2=H$, $Z_1=CH_3$, $Z_2=H$, and $Z_3=CH_3$;

2n: $X_1=X_4=F$, $X_2=X_3=X_5=H$, $Y_1=CH_3$, $Y_2=H$, $Z_1=CH_3$, $Z_2=H$, and $Z_3=CH_3$;

2o: $X_1=H$, $X_2=Cl$, $X_3=F$, $X_4=X_5=H$, $Y_1=CH_3$, $Y_2=H$, $Z_1=CH_3$, $Z_2=H$, and $Z_3=CH_3$;

2p: $X_1=F$, $X_2=H$, $X_3=Cl$, $X_4=X_5=H$, $Y_1=CH_3$, $Y_2=H$, $Z_1=CH_3$, $Z_2=H$, and $Z_3=CH_3$;

2q: $X_1=F$, $X_2=X_3=X_5=H$, $X_4=Cl$, $Y_1=CH_3$, $Y_2=H$, $Z_1=CH_3$, $Z_2=H$, and $Z_3=CH_3$;

2r: $X_1=F$, $X_2=X_3=X_5=H$, $X_4=Cl$, $Y_1=CH_3$, $Y_2=H$, $Z_1=CH_3$, $Z_2=H$, and $Z_3=CH_3$;

2s: $X_1=F$, $X_2=X_3=X_5=H$, $X_4=Cl$, $Y_1=CH_3$, $Y_2=H$, $Z_1=CH_3$, $Z_2=H$, and $Z_3=CH_3$;

2t: $X_1=X_4=X_5=H$, $X_2=Cl$, $X_3=CF_3$, $Y_1=CH_3$, $Y_2=CH_3$, $Z_1=CH_3$, $Z_2=H$, and $Z_3=CH_3$;

2u: $X_1=F$, $X_2=X_3=X_5=H$, $X_4=Cl$, $Y_1=CH_3$, $Y_2=H$, $Z_1=CH_3$, $Z_2=H$, and $Z_3=CH_3$;

2v: $X_1=F$, $X_2=X_3=X_5=H$, $X_4=Cl$, $Y_1=CH_3$, $Y_2=H$, $Z_1=CH_3$, $Z_2=H$, and $Z_3=CH_3$; or 4: $X_1=X_4=X_5=H$, $X_2=Cl$, $X_3=F$, $Y_1=NH_2$, $Y_2=H$, $Z_1=CH_3$, $Z_2=H$, and $Z_3=CH_3$.

In some embodiments, the compound is of Formula (Ib) or a pharmaceutically acceptable salt thereof:

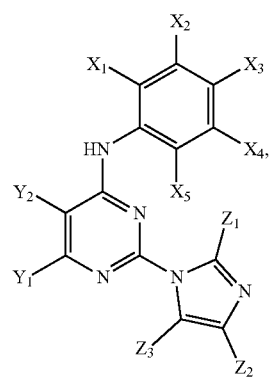

Formula (Ib)

wherein:

5a: $X_1=F$, $X_2=X_3=X_5=H$, $X_4=Cl$, $Y_1=CH_3$, $Y_2=H$, $Z_1=H$, $Z_2=CH_3$, and $Z_3=H$; or 5b: $X_1=H$, $X_2=Cl$, $X_3=F$, $X_4=X_5=H$, $Y_1=CH_3$, $Y_2=H$, $Z_1=H$, $Z_2=CH_3$, and $Z_3=H$.

In some embodiments, the compound is of Formula (Ic) or a pharmaceutically acceptable salt thereof:

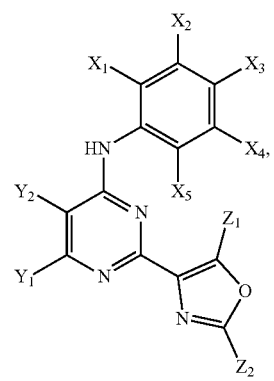

Formula (Ic)

wherein:

6a: $X_1=F$, $X_2=X_3=X_5=H$, $X_4=Cl$, $Y_1=CH_3$, $Y_2=H$, $Z_1=H$, and $Z_2=CH_3$; or 6b: $X_1=H$, $X_2=Cl$, $X_3=F$, $X_4=X_5=H$, $Y_1=CH_3$, $Y_2=H$, $Z_1=H$, and $Z_2=CH_3$.

In some embodiments, the compound is of Formula (Id) or a pharmaceutically acceptable salt there of:

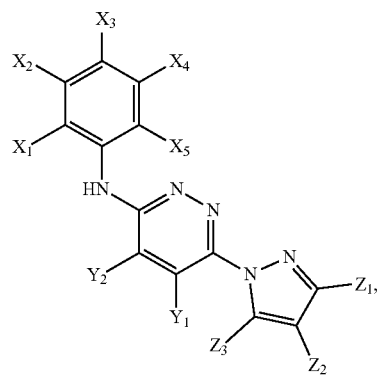

Formula (Id)

wherein:

7: $X_1=H$, $X_2=Cl$, $X_3=F$, $X_4=X_5=H$, $Y_1=H$, $Y_2=CH_3$, $Z_1=CH_3$, $Z_2=H$, and $Z_3=CH_3$.

Additional aspects of the present disclosure are directed to methods of potentiating SK channels in a subject in need thereof comprising administering a therapeutically effective amount of one or more of the foregoing compounds or one or more of the pharmaceutically acceptable salts thereof, or a pharmaceutical composition comprising one or more of the foregoing compounds or one or more of the pharmaceutically acceptable salts thereof.

In some embodiments, the subject has a movement disorder.

In some embodiments, the subject has an ataxia.

As used herein, the term "compound" is meant to include all stereoisomers, geometric isomers, tautomers, and isotopes of the structures named or depicted. Compounds herein identified by name or structure as one particular tautomeric form are intended to include other tautomeric forms unless otherwise specified.

Figure 4B:
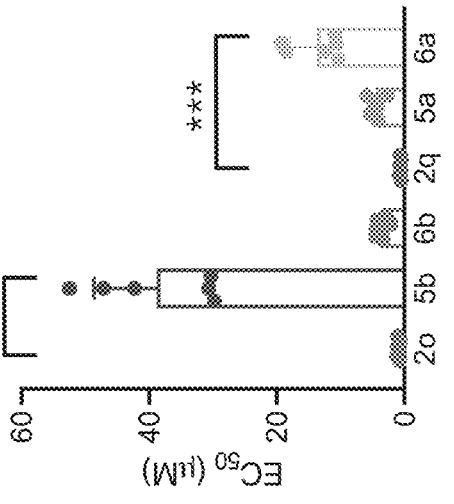
FIG. 4A-D. Optimization of the pyrazole moiety.
Figure 4D:
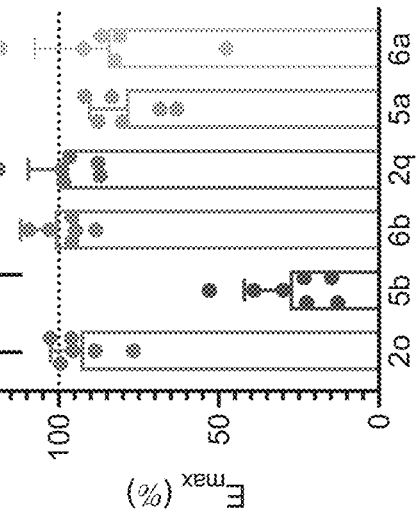
Figure 4A:
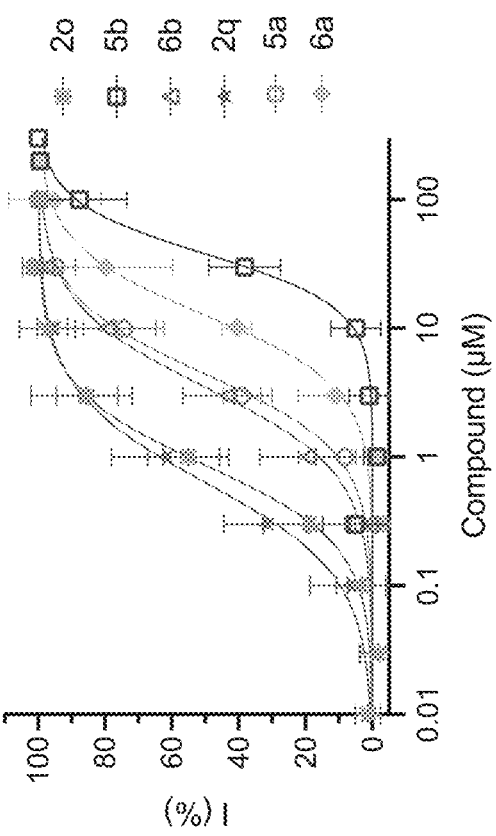

As used herein, the term "tautomer" refers to compounds which are capable of existing in a state of equilibrium between two isomeric forms. Such compounds may differ in the bond connecting two atoms or groups and the position of these atoms or groups in the compound. Suitable examples of an equilibrium between the tautomeric forms are depicted in FIGS. 4A and 4B.

As used herein, the term "isomer" refers to structural, geometric and stereo isomers. As the compound of the present disclosure may have one or more chiral centers, it is capable of existing in enantiomeric forms.

As used herein, the phrase "optionally substituted" means unsubstituted or substituted. As used herein, the term "substituted" means that a hydrogen atom is removed and replaced by a substituent. It is to be understood that substitution at a given atom is limited by valency.

As used in the present disclosure, the term "alkyl", employed alone or in combination with other terms, refers to a saturated hydrocarbon group that may be straight-chain (linear) or branched. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like.

The term "aryl," employed alone or in combination with other terms, refers to an aromatic hydrocarbon group, which may be monocyclic or polycyclic (for example, having 2, 3 or 4 fused rings). Aryl groups include, for example, phenyl, naphthyl, anthracenyl, phenanthrenyl, indanyl, indenyl and the like. In some embodiments, the aryl group is phenyl.

As used in the present disclosure, the term "alkoxy", employed alone or in combination with other terms, refers to a group of formula —O-alkyl. Exemplary alkoxy groups include, but are not limited to, methoxy, ethoxy, propoxy (for example, n-propoxy and isopropoxy), butoxy (for example, n-butoxy and tert-butoxy), and the like.

As used herein, the term "aryloxy", employed alone or in combination, refers to a group of formula —O-aryl. Exemplary aryloxy groups include, but are not limited to, phenyloxy, naphthyloxy, anthracenyloxy, phenanthrenyloxy, indanyloxy, indenyloxy and the like.

The small conductance calcium-activated potassium channels (SK channel) are a subfamily of $Ca^{2+}$-activated $K^+$ channels and the SK channel family contains 4 members- SK1, SK2, SK3, and SK4 (often referred to as intermediate conductance). The physiological roles of the SK channels have been especially studied in the nervous system, where for example they are key regulators of neuronal excitability and of neurotransmitter release, and in smooth muscle, where they are crucial in modulating the tone of vascular, broncho-tracheal, urethral, uterine or gastro-intestinal musculature.

Thus, small molecule modulators of potassium ion channels could have the potential to treat a large variety of diseases characterized by dysfunction of potassium ion channels and dysfunction from other causes which influence these potassium channels.

In some embodiments, compounds and compositions described herein are useful in treating diseases and/or disorders associated with the activity of potassium channels. Such diseases and/or disorders include e.g., neurodegenerative and neurological conditions (e.g., Parkinson's disease, tremors, Alzheimer's disease, dementia, amyotrophic lateral sclerosis (ALS) ataxia, anxiety, depression, mood disorders, memory and attention deficits, bipolar disorder, psychosis, schizophrenia, traumatic brain injury, and narcolepsy), heart disease and related conditions (e.g., ischemic heart disease, coronary heart disease, angina pectoris, and coronary artery spasms), metabolic disease and bladder diseases (e.g., bladder spasms, urinary incontinence, bladder outflow obstruction, gastrointestinal dysfunction, irritable bowel syndrome, and diabetes), withdrawal symptoms associated with termination of addiction, and other conditions associated with the modulation of potassium channels such as e.g., respiratory diseases, epilepsy, convulsions, seizures, absence seizures, vascular spasms, renal disorders (e.g., polycystic kidney disease), erectile dysfunction, secretory diarrhea, ischemia, cerebral ischemia, dysmenorrhea, Reynaud's disease, intermittent claudication, Sjorgren's syndrome, arrhythmia, hypertension, myotonic muscle dystrophia, spasticity, xerostomi, hyperinsulinemia, premature labor, baldness, cancer, immune suppression, migraine and pain.

The present disclosure also provides a method of modulating the activity of a potassium channel in a subject comprising the step of administering a compound described herein. In another embodiment, the present disclosure provides a method of positively modulating a SK channel in a cell comprising the step of contacting the cell with a compound described herein.

In one aspect, the provided compounds and compositions are used to treat tremors. Tremors include, but are not limited to rest, active, postural, kinetic, intention, task specific, and idiopathic tremors. In one aspect, the provided compounds and compositions are used to treat postural and active tremors. Examples of postural and/or active tremors include essential tremor, drug-induced parkinsonism, neuropathic tremor, and tremors induced from toxins (e.g., alcohol withdrawal or from exposure to heavy metals). In one aspect, the provided compounds and compositions are used to treat essential tremor.

The present disclosure further provides a method of treating essential tremor in a subject comprising the step of administering a compound or pharmaceutically acceptable salt or composition described herein.

Essential tremor is one of the most common neurological disorders, affecting ~0.9% of the general population. Essential tremor is characterized by an action tremor of the upper limbs and, less commonly, the head, voice, and trunk. A family history of essential tremor can be identified in approximately half of patients, suggesting a genetic component. Drinking alcohol often temporarily reduces tremor.

In some embodiments, the present disclosure provides a method of treating a disease or condition selected from a neurodegenerative disease, dementia, and heart disease, withdrawal symptoms associated with termination of addiction, metabolic disease, and bladder disease. In other embodiments, the present disclosure provides a method of treating a disease or condition selected from ataxia, dystonia, Parkinson's disease, ischemia, traumatic brain injury, amyotrophic lateral sclerosis, hypertension, atherosclerosis, diabetes, arrhythmia, over-active bladder, and withdrawal symptoms caused by the termination of abuse of alcohol and other drugs of abuse. In some embodiments, the present disclosure provides a method of treating ataxia. In some embodiments, the present disclosure provides a method of treating spinocerebellar ataxia.

The terms "pharmaceutical" and "pharmaceutically acceptable" are employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "individual", "patient", or "subject" used interchangeably, refers to any animal, including mammals, preferably mice, rats, other rodents, rabbits, dogs, cats, swine, cattle, sheep, horses, or primates, and most preferably humans.

As used herein, the phrase "effective amount" or "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "preventing" or "prevention" of a disease, condition or disorder refers to decreasing the risk of occurrence of the disease, condition or disorder in a subject or group of subjects (e.g., a subject or group of subjects predisposed to or susceptible to the disease, condition or disorder). In some embodiments, preventing a disease, condition or disorder refers to decreasing the possibility of acquiring the disease, condition or disorder and/or its associated symptoms. In some embodiments, preventing a disease, condition or disorder refers to completely or almost completely stopping the disease, condition or disorder from occurring.

As used herein, in such methods the term "biological sample" refers to a body fluid or tissue. The body fluid can include, without limitation, whole blood, serum, plasma, peripheral blood, synovial fluid, cerebrospinal fluid, saliva, urine, semen, or other fluid secretion. The term "tissue" can include, without limitation, bone marrow and lymph node, as well as samples of other tissues.

The present disclosure also provides pharmaceutical compositions comprising an effective amount of a compound of Formula (I) disclosed herein, or a pharmaceutically acceptable salt thereof; and a pharmaceutically acceptable carrier. In certain embodiments, the disclosure also provides pharmaceutical compositions and dosage forms comprising any one the additional therapeutic agents described herein. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of the present disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The compositions or dosage forms may contain any one of the compounds and therapeutic agents described herein in the range of 0.005% to 100% with the balance made up from the suitable pharmaceutically acceptable excipients. The contemplated compositions may contain 0.001%-100% of any one of the compounds and therapeutic agents provided herein, in one embodiment 0.1-95%, in another embodiment 75-85%, in a further embodiment 20-80%, wherein the balance may be made up of any pharmaceutically acceptable excipient described herein, or any combination of these excipients.

Routes of Administration and Dosage Forms

The pharmaceutical compositions of the present disclosure include those suitable for any acceptable route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intranasal, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

Compositions and formulations described herein may conveniently be presented in a unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, MD (20th ed. 2000). Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product. Also, see, for example, Ansel's Pharmaceutical Dosage Forms and Drug Delivery Systems, Wolters Kluwer Health (11th ed. 2018).

In some embodiments, any one of the compounds and therapeutic agents disclosed herein are administered orally. Compositions of the present disclosure suitable for oral administration may be presented as discrete units such as capsules, sachets, granules or tablets each containing a predetermined amount (e.g., effective amount) of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption. In the case of tablets for oral use, carriers that are commonly used include lactose, sucrose, glucose, mannitol, and silicic acid and starches. Other acceptable excipients may include: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added. Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions or infusion solutions which may contain antioxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, saline (e.g., 0.9% saline solution) or 5% dextrose solution, immediately prior to use. Extemporaneous injection solutions and suspensions may be prepared from sterile powders, granules and tablets. The injection solutions may be in the form, for example, of a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (e.g., glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

The pharmaceutical compositions of the present disclosure may be administered in the form of suppositories for rectal administration. These compositions can be prepared by mixing a compound of the present disclosure with a suitable non-irritating excipient which is solid at room temperature but liquid at the rectal temperature and therefore will melt in the rectum to release the active components. Such materials include, but are not limited to, cocoa butter, beeswax, and polyethylene glycols.

The pharmaceutical compositions of the present disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031. Additional formulations and methods for intranasal administration are found in Ilium, L., *J Pharm Pharmacol,* 56:3-17, 2004 and Ilium, L., *Eur J Pharm Sci* 11:1-18, 2000.

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form. Topical administration of the pharmaceutical compositions of the present disclosure is especially useful when the desired treatment involves areas or organs readily accessible by topical application. In some embodiments, the topical composition comprises a combination of any one of the compounds and therapeutic agents disclosed herein, and one or more additional ingredients, carriers, excipients, or diluents including, but not limited to, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

Examples of useful dermatological compositions which can be used to deliver the compounds to the skin are known in the art; see for example, Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The compounds and therapeutic agents of the present disclosure may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the present disclosure provides an implantable drug release device impregnated with or containing a compound or a therapeutic agent, or a composition comprising a compound of the present disclosure or a therapeutic agent, such that said compound or therapeutic agent is released from said device and is therapeutically active.

Dosages and Regimens

In the pharmaceutical compositions of the present disclosure, a compound of Formula (I) is present in an effective amount (e.g., a therapeutically effective amount).

Effective doses may vary, depending on the diseases treated, the severity of the disease, the route of administration, the sex, age and general health condition of the subject, excipient usage, and the possibility of co-usage with other therapeutic treatments such as use of other agents and the judgment of the treating physician.

In some embodiments, an effective amount of a compound of Formula (I) can range, for example, from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 2 mg/kg; from about 0.1 mg/kg to about 1 mg/kg; or from about 0.1 mg/kg to about 0.5 mg/kg).

In some embodiments, an effective amount of a compound of Formula (I) is about 0.1 mg/kg, about 0.5 mg/kg, about 1 mg/kg, about 2 mg/kg, or about 5 mg/kg.

The foregoing dosages can be administered on a daily basis (e.g., as a single dose or as two or more divided doses, e.g., once daily, twice daily, thrice daily) or non-daily basis (e.g., every other day, every two days, every three days, once weekly, twice weekly, once every two weeks, once a month).

EXAMPLES

Example 1

1. Chemistry

The chemical structure of the template, CyPPA is shown in Scheme 1. Scheme 1 depicts the synthesis of 4-amino-substituted analogs of 2-(3,5-dimethyl-1H-pyrazol-1-yl)-6-methylpyrimidine (2a-f) using 4-substituted cyclohexan-1-amine and 4-chloro-2-(3,5-dimethyl-1H-pyrazol-1-yl)-6-methylpyrimidine (1a). Compound 1a underwent nucleophilic substitution reaction via its reaction with the corresponding 4-substituted cyclohexan-1-amine in anhydrous N,N-dimethylformamide (DMF) in the presence of N,N-diisopropylethylamine (DIPEA) at room temperature to afford 2a-f in 77-84% yield.

The reaction of 1a with 2-(4-nitrophenyl) ethan-1-amine and tyrosine analogues under a similar condition afforded compounds 2g-j in 72-75% yield (Scheme 1).

Scheme 2 shows the synthesis of 4-aniline substituted analogs of 2-(3,5-dimethyl-1H-pyrazol-1-yl)-6-methylpyrimidine (2k-v) (47-83%) through the reaction of 1a with different aniline derivatives in the presence of DIPEA and refluxing at 95° C. in DMF. Compound 2w was also synthesized under the same conditions described for the synthesis of compounds 2k-v by the reaction of 1a and 5,6-dimethoxy-2H-benzo[d]imidazol-2-amine.

Scheme 1. Synthesis of CyPPA analogs (2a-j)
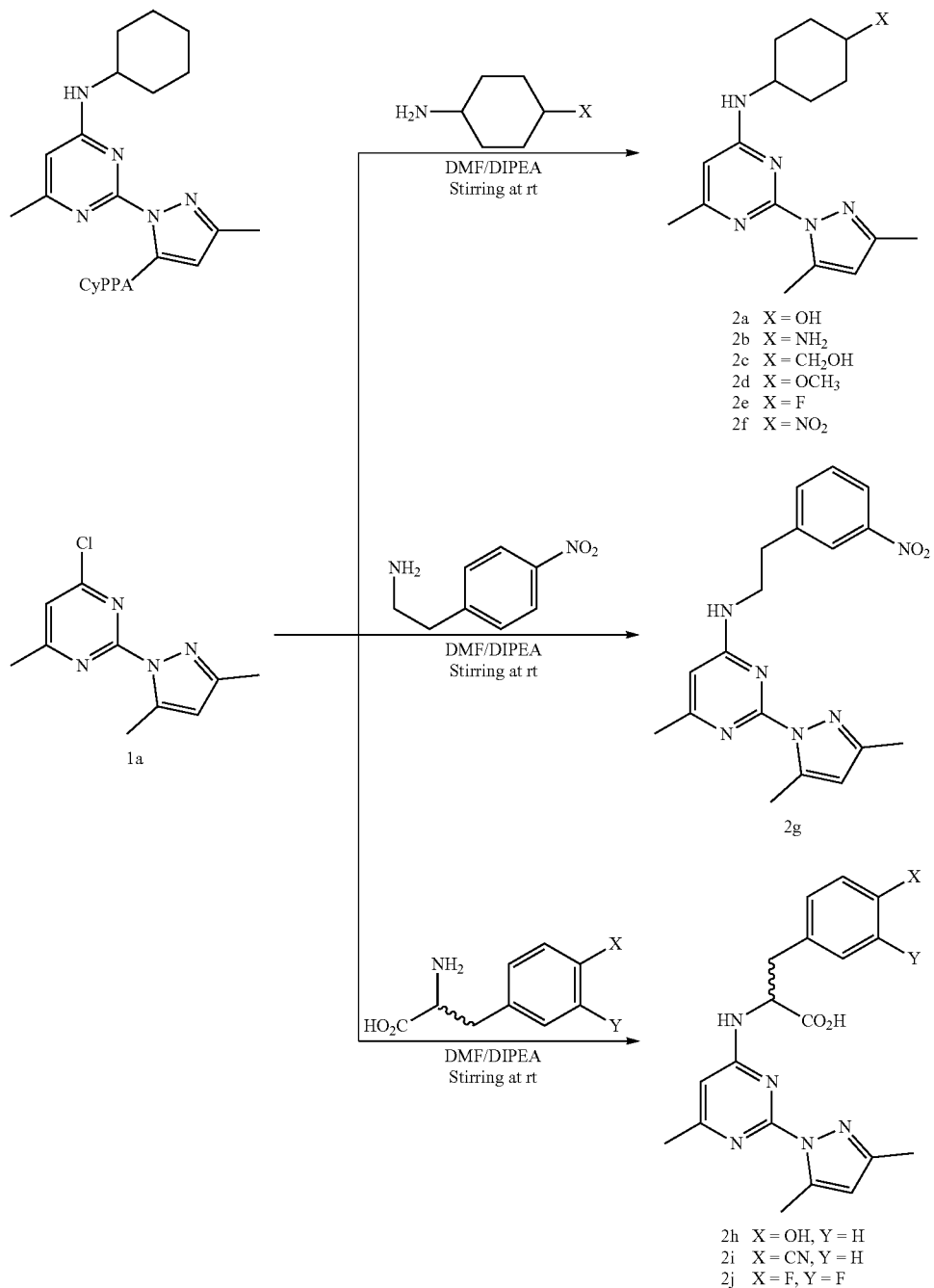

Scheme 2. Synthesis of CyPPA analogs 2k-w.

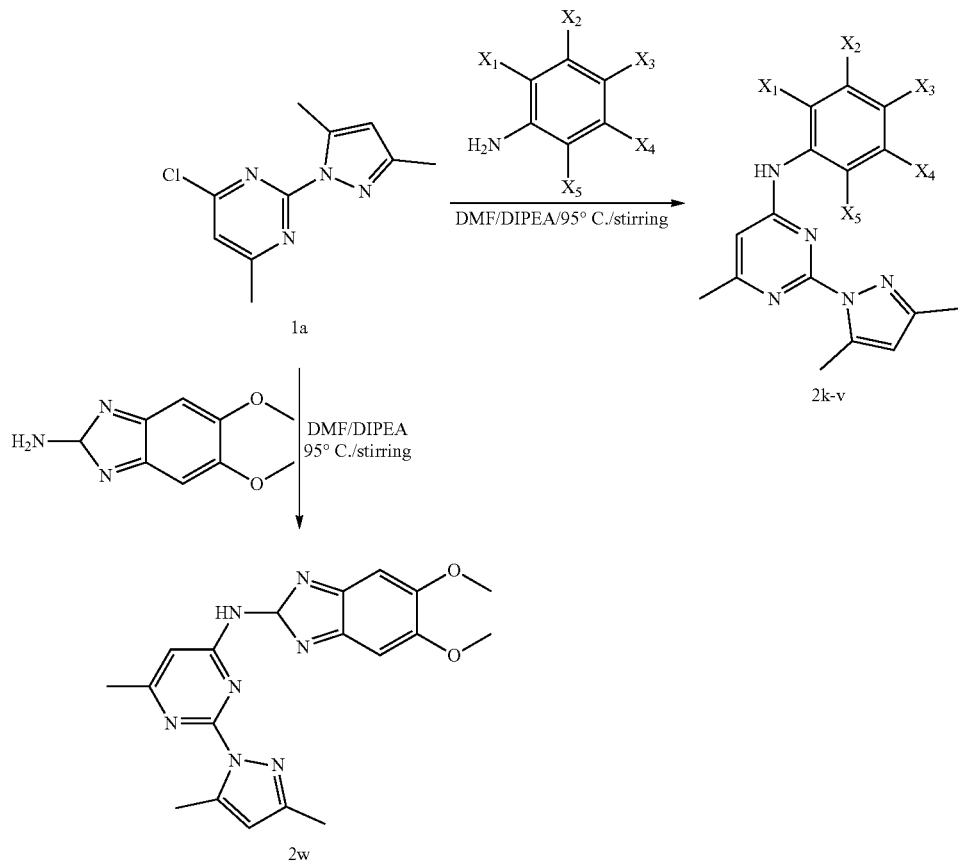

2k  $X_1 = X_2 = X_4 = X_5 = H, X_3 = SH$
2l  $X_1 = X_2 = X_4 = X_5 = H, X_3 = NO_2$
2m  $X_1 = F, X_2 = F, X_3 = X_4 = X_5 = H$
2n  $X_1 = F, X_2 = X_3 = H, X_4 = F, X_5 = H$
2o  $X_1 = H, X_2 = Cl, X_3 = F, X_4 = X_5 = H$
2p  $X_1 = F, X_2 = H, X_3 = Cl, X_4 = X_5 = H$
2q  $X_1 = F, X_2 = X_3 = H, X_4 = Cl, X_5 = H$
2r  $X_1 = Cl, X_2 = X_3 = H, X_4 = F, X_5 = H$
2s  $X_1 = X_2 = H, X_3 = CF_3, X_4 = X_5 = H$
2t  $X_1 = H, X_2 = Cl, X_3 = CF_3, X_4 = X_5 = H$
2u  $X_1 = H, X_2 = Cl, X_3 = H, X_4 = CF_3, X_5 = H$
2v  $X_1 = F, X_2 = X_3 = H, X_4 = CO_2H, X_5 = H$

Furthermore, the impact of changing the position of the 3,5-dimethylpyrazole ring and replacing the methyl group with an amino group on the pyrimidine was investigated by replacing (1a) with 4-chloro-6-(3,5-dimethyl-1H-pyrazol-1-yl)pyrimidin-2-amine (1b) and its coupling with different halogen-substituted aniline derivatives affording compounds 3a-g. In the same context, the 4-amino analog of 6-chloro-2-(3,5-dimethyl-1H-pyrazol-1-yl)pyrimidine-4-amine (1c) reacted with 3-chloro-4-fluoroaniline, yielding compound 4. Likewise, compounds 5a-b, 6a-b, and 7 were synthesized as described in Scheme 3 from the reaction of appropriate anilino-substituted analogs 4-chloro-6-methyl-2-(4-methyl-1H-imidazol-1-yl)pyrimidine (1d), 4-(4-chloro-6-methylpyrimidin-2-yl)-2-methyloxazole (1e), in which the pyrazole moiety was replaced by imidazolyl (1d) and oxazolyl (1e) moieties, or replacing the pyrimidine ring with pyridazine ring as in 3-chloro-6-(3,5-dimethyl-1H-pyrazol-1-yl)-4-methylpyridazine (1f).

Scheme 3. Synthesis of CyPPA analogs (3-7).
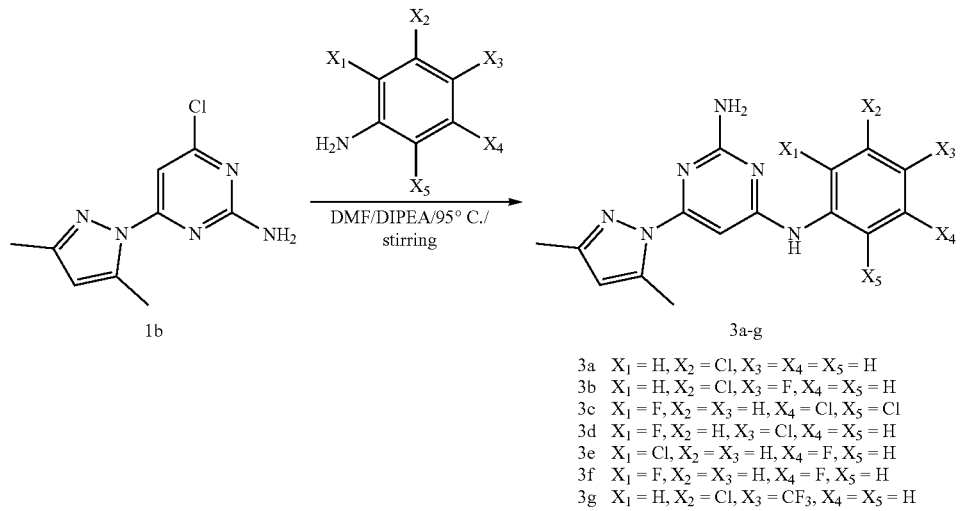
3a  $X_1 = H, X_2 = Cl, X_3 = X_4 = X_5 = H$
3b  $X_1 = H, X_2 = Cl, X_3 = F, X_4 = X_5 = H$
3c  $X_1 = F, X_2 = X_3 = H, X_4 = Cl, X_5 = Cl$
3d  $X_1 = F, X_2 = H, X_3 = Cl, X_4 = X_5 = H$
3e  $X_1 = Cl, X_2 = X_3 = H, X_4 = F, X_5 = H$
3f  $X_1 = F, X_2 = X_3 = H, X_4 = F, X_5 = H$
3g  $X_1 = H, X_2 = Cl, X_3 = CF_3, X_4 = X_5 = H$
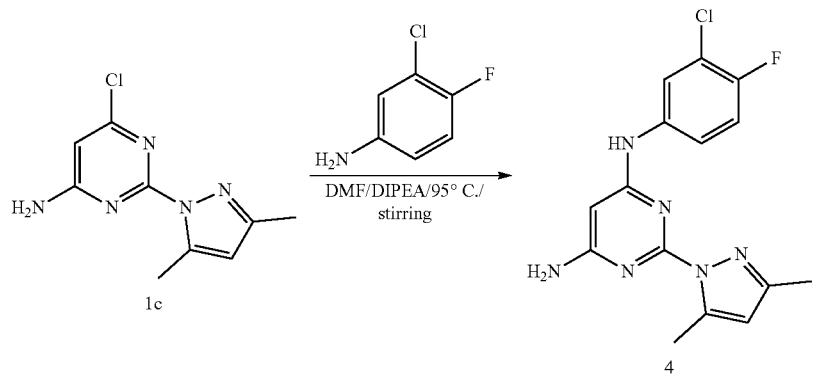
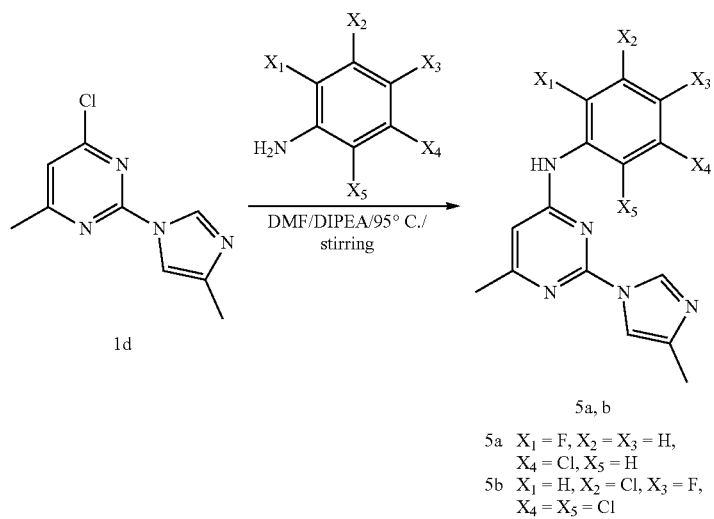
5a  $X_1 = F, X_2 = X_3 = H,$
    $X_4 = Cl, X_5 = H$
5b  $X_1 = H, X_2 = Cl, X_3 = F,$
    $X_4 = X_5 = Cl$ -continued

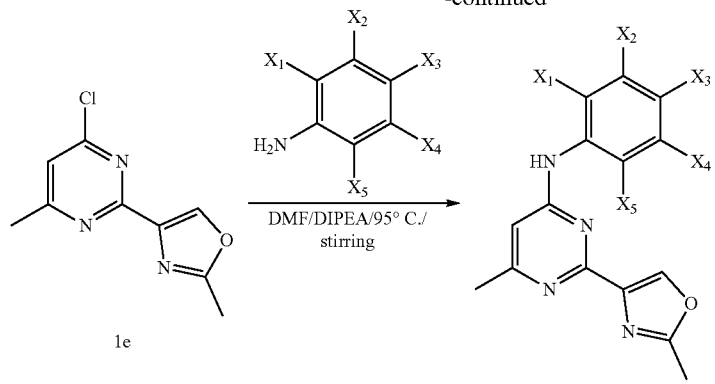

6a, b

6a $X_1 = F, X_2 = X_3 = H,$
$X_4 = Cl, X_5 = H$
6b $X_1 = H, X_2 = Cl, X_3 = F,$
$X_4 = X_5 = Cl$

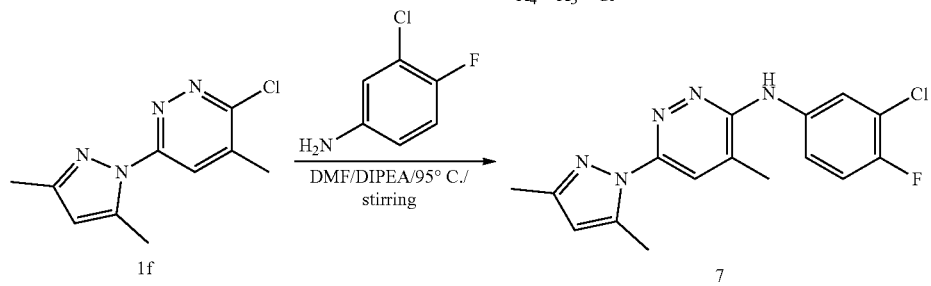

2. Structure-Activity Relationship

The activity of the compounds on potentiating $K_{Ca}2.2a$ channels is summarized in Table 1. The structure-activity relationship of the compounds was evaluated by considering the effect of functional group modifications in the CyPPA template. CyPPA has an $EC_{50}$ value of 7.48±0.56 µM (n=8).
Table 1. The potency of compounds on potentiating $K_{Ca}2.2a$ channels compared to the parent template, CyPPA.

| Compound | $EC_{50}$ (mean ± SEM, µM) |
|---|---|
| CyPPA | 7.48 ± 0.56 |
| 2a | >100 |
| 2b | >100 |
| 2c | >100 |
| 2d | 49.72 ± 4.38 |
| 2e | >100 |
| 2f | >100 |
| 2g | >100 |
| 2h | >100 |
| 2i | >100 |
| 2j | >100 |
| 2k | >100 |
| 2l | >100 |
| 2m | 5.03 ± 0.59 |
| 2n | 1.89 ± 0.16 |
| 2o | 0.99 ± 0.079 |
| 2p | 1.99 ± 0.11 |
| 2q | 0.64 ± 0.051 |
| 2r | 2.97 ± 0.27 |
| 2s | 3.45 ± 0.42 |
| 2t | 3.27 ± 0.30 |
| 2u | >100 |
| 2v | 37.60 ± 3.66 |
| 2w | >100 |
| 3a | >100 |
| 3b | >100 |
| 3c | >100 |
| 3d | >100 |
| 3e | >100 |
| 3f | >100 |
| 3g | >100 |
| 4 | 6.59 ± 0.64 |
| 5a | 4.51 ± 0.44 |
| 5b | 38.81 ± 4.02 |
| 6a | 13.77 ± 1.68 |
| 6b | 3.59 ± 0.33 |
| 7 | 4.32 ± 0.32 |

Optimization of the Cyclohexane/Phenyl Moiety

The impact of adding one substituent group at C4 of the cyclohexane moiety of CyPPA with either electron donating (OH (2a), $NH_2$ (2b), $CH_2OH$ (2c), and $OCH_3$ (2d)) or electron-withdrawing groups (F (2e) and $NO_2$ (2f)) was explored. The potency of the newly synthesized compounds compared to the template CyPPA was measured via inside-out patch clamp electrophysiology recordings with $K_{Ca}2.2a$ channels heterologously expressed in HEK293 cells (FIG. 1A). Among these compounds, only compound 2d with the methoxy group was able to potentiate the $K_{Ca}2.2$ channel with a drastically larger $EC_{50}$ value of 49.72±4.38 µM (n=9), compared with the $EC_{50}$ value of 7.48±0.56 µM for CyPPA (FIG. 1B). All other compounds were inactive on the $K_{Ca}2.2a$ channel. The responses induced by 10 µM $Ca^{2+}$ are considered the maximal currents of the $K_{Ca}2.2a$ channels. To evaluate the efficacy ($E_{max}$) of compounds on $K_{Ca}2.2a$ channels, the current amplitudes at −90 mV in response to the maximal concentration of compounds were normalized to that obtained at 10 μM Ca$^{2+}$ (I/I$_{max}$ (%), FIG. 1C). Compound 2d exhibited an E$_{max}$ of 77.30±4.95% (n=9) on K$_{Ca}$2.2a channels, which is comparable to the E$_{max}$ of 82.41±4.91% (n=8) of CyPPA (FIG. 1D).

Figure 2C:
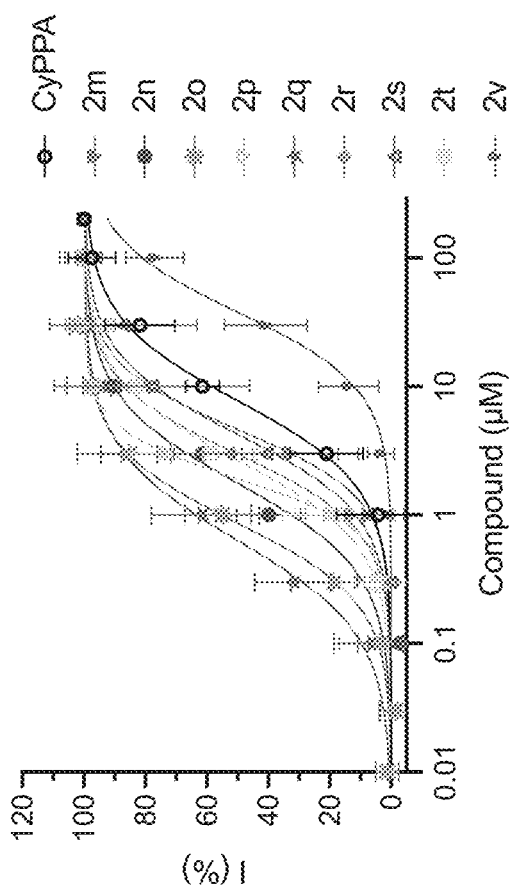
Figure 2D:
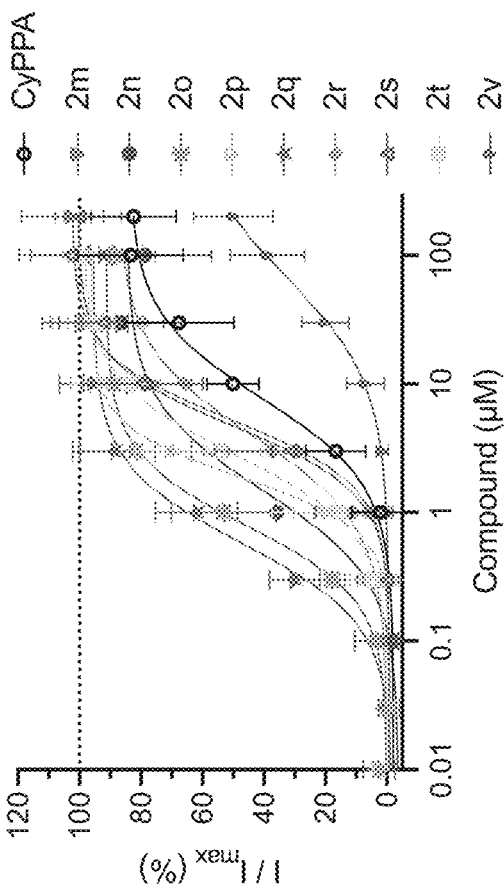

The binding pocket for CyPPA between CaM C-lobe and the HA/HB helices in K$_{Ca}$2.2a channels was identified. The binding interface between CaM and its substrates are largely hydrophobic. As such, the cyclohexane moiety was replaced with more hydrophobic monosubstituted and disubstituted phenyl groups and decorated with one or more electron withdrawing groups, such as trifluoromethane, nitro, carboxylic or hydrogen sulfide groups. Compounds 2k and 2l with a thiol or nitro substitution on the phenyl ring, respectively, were inactive. Compound 2v, which has carboxylic acid and fluoro substituents, potentiated K$_{Ca}$2.2a channels with a reduced potency of 37.6±3.66 μM (n=5) (FIGS. 2A and B). It is noted that 2v did not seem to have achieved its maximal response on K$_{Ca}$2.2a channels due to its limited solubility at 200 μM. Compound 2v exhibited reduced efficacy with an E$_{max}$ value of 50.01±5.78% (n=5) (FIGS. 2C and D). As such, its real potency could have been even more reduced. A single 4-trifluoromethane substituent (2s) did not significantly change the potency compared with CyPPA, with EC$_{50}$ value of 3.45±0.42 μM (n=6) (FIGS. 2A and B). The potency of dihalogen substituted phenyl derivatives (2n-r and 2t) significantly increased compared with CyPPA (FIGS. 2A and B). Among them, compounds (2q) potentiated K$_{Ca}$2.2 channels with an EC$_{50}$ value of 0.64±0.051 μM (n=6), which is ~10-fold more potent than CyPPA. The EC$_{50}$ value of (2o) is 0.99±0.079 μM (n=6), which is ~7-fold more potent than CyPPA. All of these compounds exhibited similar efficacy (E$_{max}$) on K$_{Ca}$2.2a channels as CyPPA, except for (2v) which had reduced efficacy (FIGS. 2C and D). Thus, improvement of potency was achieved through halogen substitutions on the phenyl ring; dihalogen substitutions at the positions 2 and 5 or 3 and 4 of the phenyl ring especially induced ~10- and ~7-fold increases in potency, respectively.

Optimization of the Linker Between Pyrimidine and Phenyl

In the structure of CyPPA, the pyrimidine is connected to the cyclohexane ring through an ethylene linker. Replacing the hydrogen atom with an α-carboxylic group, in addition to replacing the cyclohexane with substituted phenyl groups (2h-j), resulted in the loss of activity on the K$_{Ca}$2.2a channel.

Optimization of the Pyrimidine Moiety

Figure 3A:
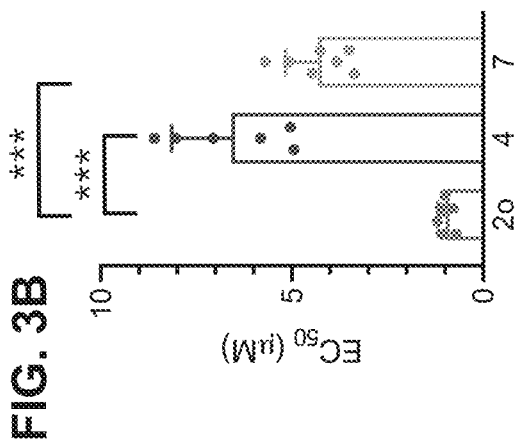
FIG. 3A-D. Optimization of the pyrimidine moiety.
Figure 3B:
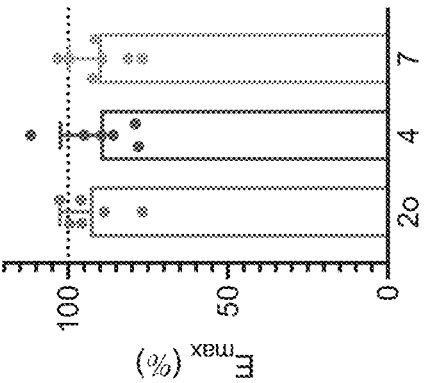
Figure 3C:
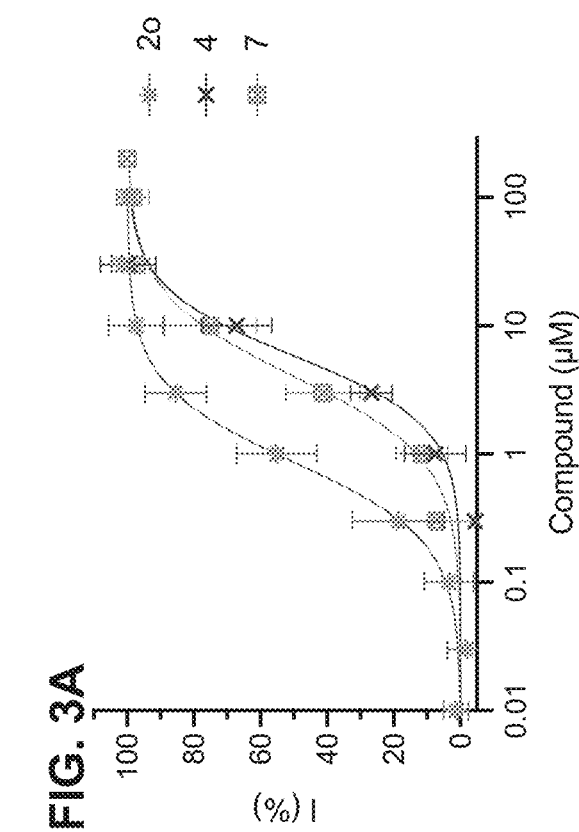
Figure 3D:
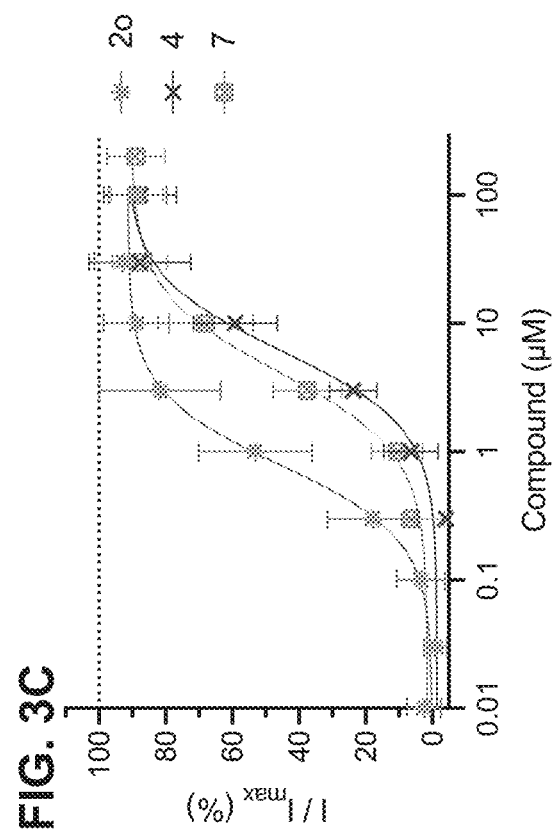

Since 2o has achieved ~7-fold better potency than CyPPA, 2o was used as a template for further optimization of the affording pyrimidine moiety. Changing the position at which the dimethyl pyrazole moiety is attached from C2 to C6 and replacing the methyl group with amino group as in compound 1b, resulted in a loss of activity for compounds 3a-g. Compounds 3a-g were inactive on the K$_{Ca}$2.2 channel. Replacing the methyl group at C6 of the pyrimidine moiety with an amine afforded compound 4. The replacement of pyrimidine ring with a piperazine ring generated compound 7. Both compounds 4 and 7 exhibited reduced potency (FIGS. 3A and B), while retaining their efficacy (FIGS. 3C and D).

Optimization of the Pyrazole Moiety

Figure 4C:
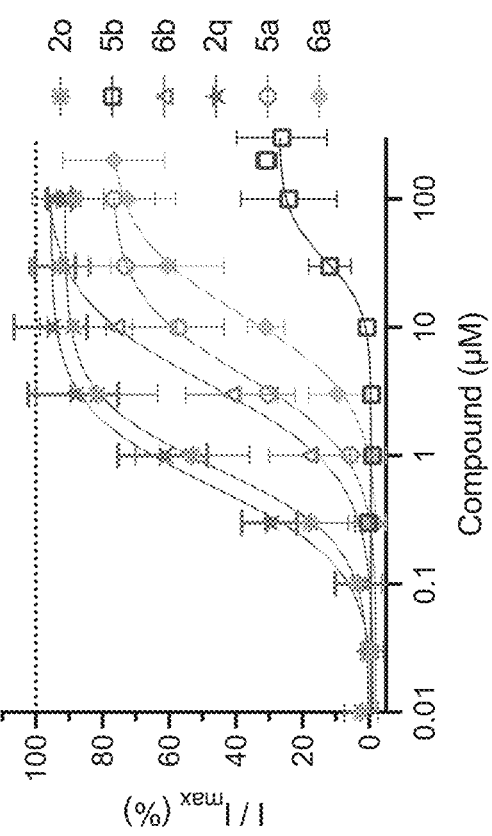

Compounds 2o and 2q were used as templates for further structure optimization of the pyrazole moiety. The effect of replacing the pyrazole moiety with other five membered heterocyclic ring systems was investigated to determine whether the pyrazole ring is required for the potentiation of K$_{Ca}$2.2a channels by CyPPA. When the pyrazole ring was replaced by an imidazole ring, the resulting compounds were 5a and 5b. The replacement of the pyrazole ring with an oxazole afforded compounds 6a and 6b. Compound 6a exhibited lower potency than 2q on potentiating K$_{Ca}$2.2a channels, whereas the potency of 5b was drastically reduced compared with 2o (FIGS. 4A and B). Compounds 5a, 6a, and 6b retained their efficacy, while the E$_{max}$ value of 5b was decreased compared with 2o (FIGS. 4C and D).

Channel Subtype Selectivity of the New Compounds

Figure 5A:
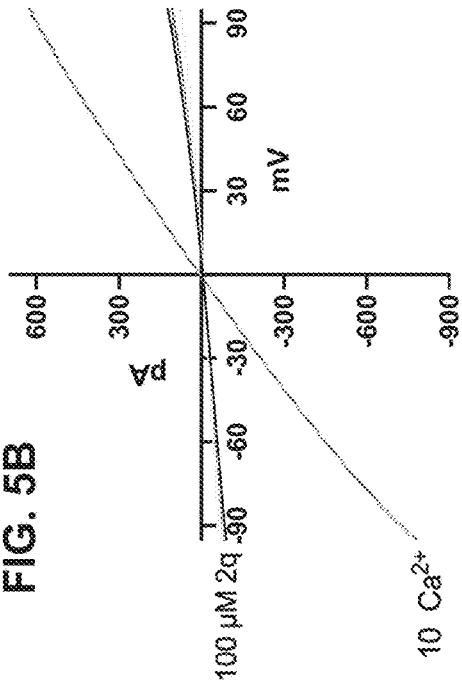
FIG. 5A-D. Subtype-selectivity towards $K_{Ca}2.2a$ over $K_{Ca}2.1$ channels.
Figure 5C:
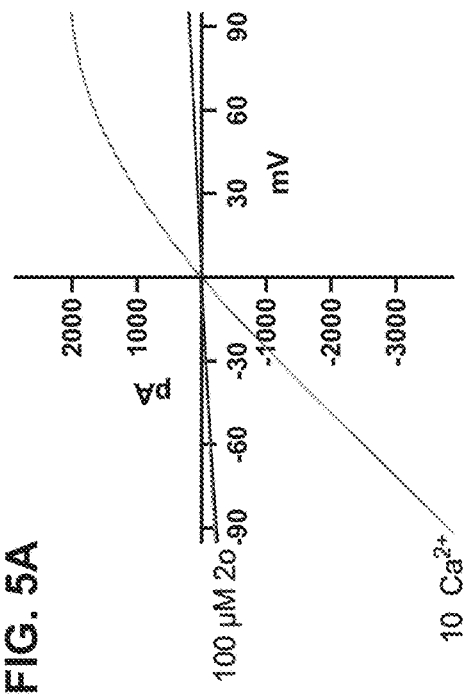
Figure 5B:
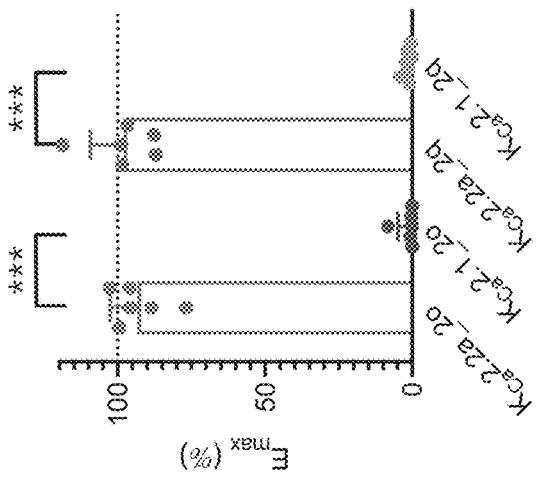
Figure 5D:
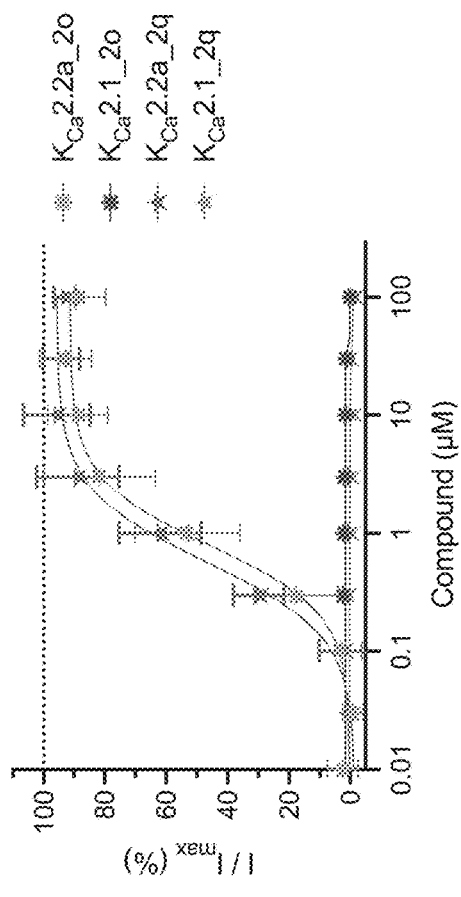
Figure 6B:
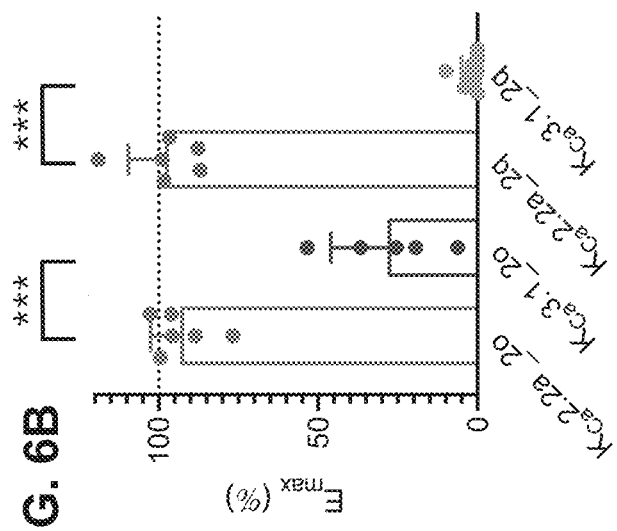
FIG. 6A-B. Subtype-selectivity towards $K_{Ca}2.2a$ over $K_{Ca}3.1$ channels.
Figure 6A:
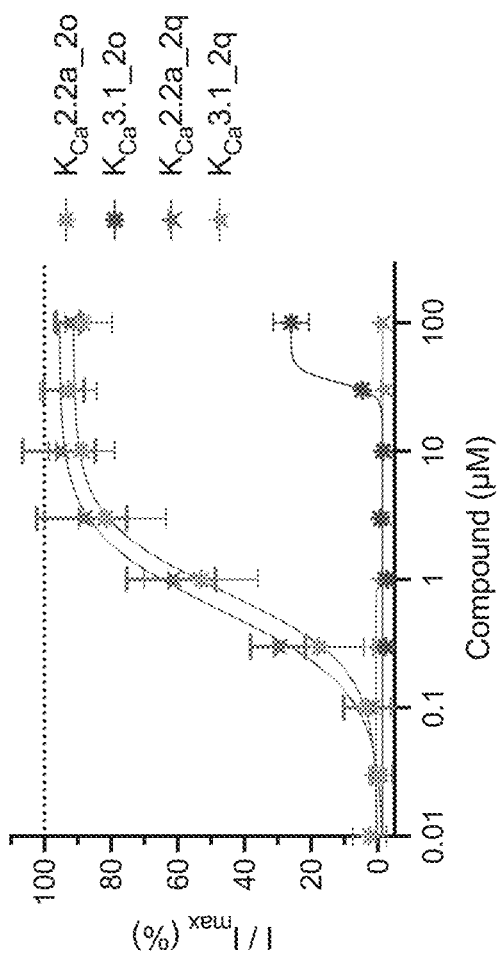

As described above, 3-chloro-4-fluorophenyl and 5-chloro-2-fluorophenyl disubstituted 4-aniline substituted analogs of 2-(3,5-dimethyl-1H-pyrazol-1-yl)-6-methylpyrimidine (2o and 2q) were the most potent CyPPA analogs. CyPPA selectively potentiates K$_{Ca}$2.2a and K$_{Ca}$2.3, but not K$_{Ca}$2.1 and K$_{Ca}$3.1 channel subtypes. The two newly synthesized compounds, 2o and 2q, were tested to determine whether they retained their subtype-selectivity. Neither 2o (FIG. 5A) nor 2q (FIG. 5B) elicited significant responses from the human K$_{Ca}$2.1 channel expressed in HEK293 cells. When compared with the responses from K$_{Ca}$2.2a channels to these two compounds, the differences became even more apparent (FIG. 5C), with the E$_{max}$ values on K$_{Ca}$2.2a channels at ~90%, whereas the E$_{max}$ values on K$_{Ca}$2.1 channels were at ~0% (FIG. 5D). Similarly, the human K$_{Ca}$3.1 channel expressed in HEK293 cells was mostly insensitive to the two newly synthesized compounds (FIG. 6A). The E$_{max}$ value of 2o on K$_{Ca}$3.1 channels was 26.14±7.67% (n=5) whereas the E$_{max}$ value of 2q on K$_{Ca}$3.1 channels was −0.79±1.19% (n=10) (FIG. 6B).

CyPPA has a slightly but significantly higher potency on K$_{Ca}$2.3 channels than K$_{Ca}$2.2a channels. The effects of the two newly synthesized compounds on human K$_{Ca}$2.3 channels (FIG. 7A) were examined. Compound 2o potentiated K$_{Ca}$2.3 channels with an EC$_{50}$ value of 0.19±0.023 μM (n=10), which was significantly smaller than its EC$_{50}$ value of 0.99±0.079 μM (n=6) on the K$_{Ca}$2.2 channel subtype. In contrast, 2q exhibited similar potency on the K$_{Ca}$2.2a and K$_{Ca}$2.3 channel subtypes, with EC$_{50}$ values of 0.64±0.051 μM (n=6) and 0.60±0.035 μM (n=9), respectively (FIG. 7B). The E$_{max}$ values of 2o and 2q were similar between the K$_{Ca}$2.2a and K$_{Ca}$2.3 channel subtypes (FIGS. 7C and D).

Figure 8A:
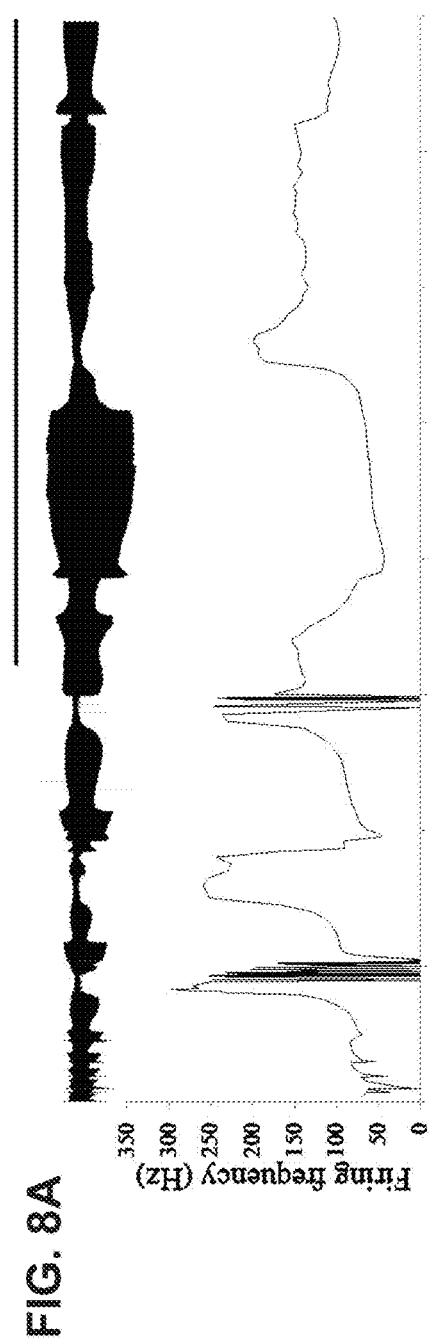
FIG. 8A-C. Non-selective $K_{Ca}2.x/K_{Ca}3.1$ channel positive modulator chlorzoxazone (CHZ) converts bursting patterns into tonic activity of PC in acute cerebellar slices from 8-mo-old SCA2-58Q mouse.
Figure 8B:
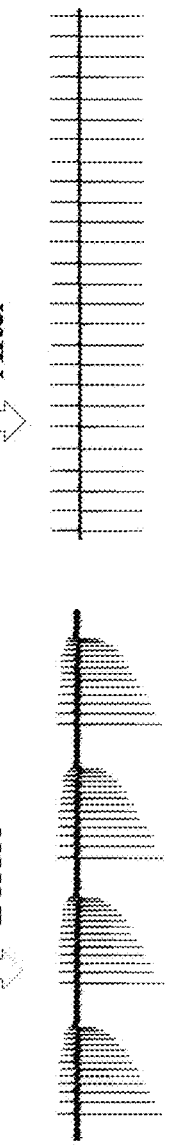

Normalization of Cerebellar PC Firing from SCA2-58Q Transgenic Mice by the New Compounds The accurate firing of the cerebellar Purkinje cells (PCs) is crucial for proper cerebellar functioning. In the mouse model of SCA2, aging SCA2-58Q transgenic mice, the gradually increasing portion of PCs with highly irregular bursting activity was observed. Consistent with the preceding results, in the current study, most of PCs from 7-8 months old WT mice (97±2%, n=56 PCs) were firing tonically (examples of tonic patterns: FIG. 8B right; FIG. 9B right; and FIG. 10B right), whereas much fewer PCs from SCA2 mice of the same age were having stable firing rates (75±4%, n=119 PCs, **p<0.01). Thus, every fourth SCA2-58Q PC cell exhibited bursting activity patterns (FIG. 8B left; FIG. 9B left; and FIG. 10B left). The highly irregular bursting activity reflects the consequences of the ionic imbalance observed in SCA2 PCs, leading to the motor decline in SCA2 mice. Thus, the compounds that can convert bursting activity into the tonic mode have the potential therapeutic effect for SCA2 and other ataxias.

Figure 8C:
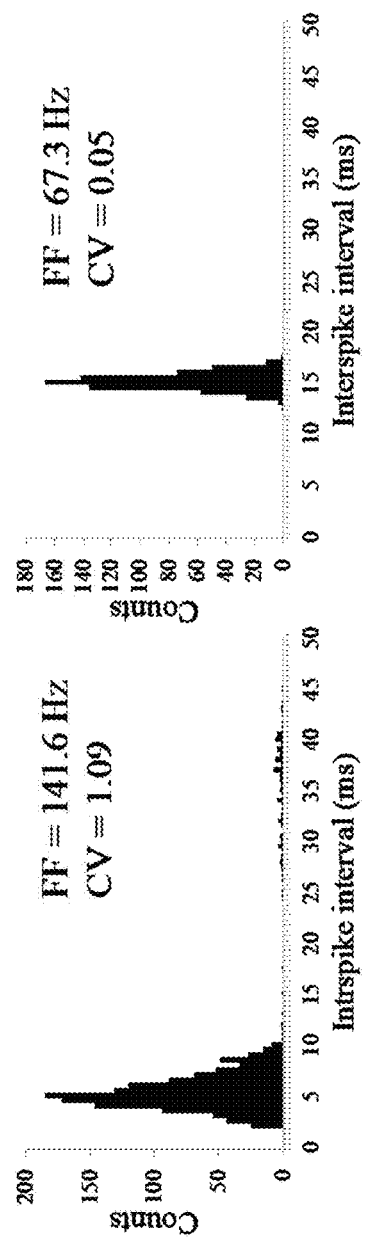
Figure 10A:
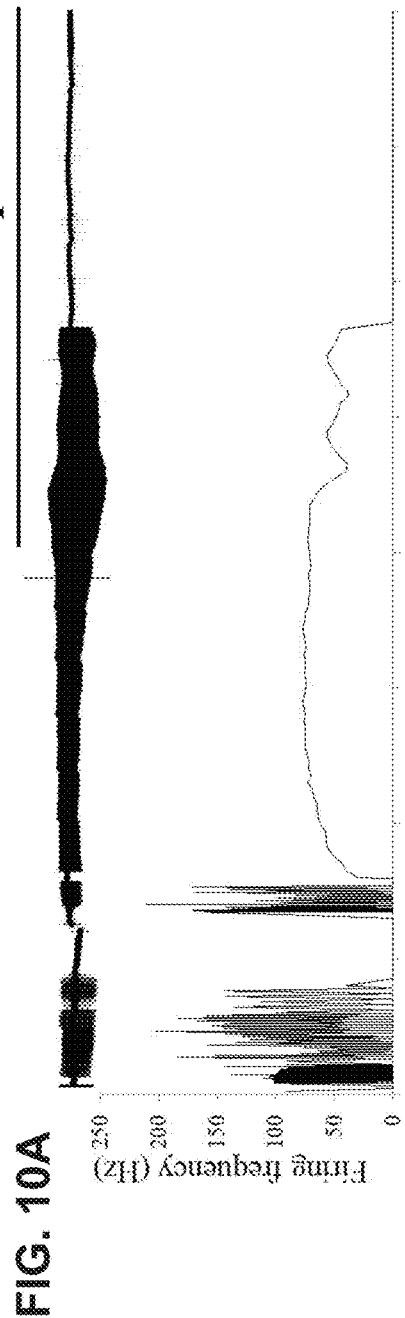
FIG. 10A-C. Subtype-selective $K_{Ca}2.2/K_{Ca}2.3$ channel positive allosteric modulator 2q converts bursting patterns into tonic activity of PC and then into a silent mode in acute cerebellar slices from 8-mo-old SCA2-58Q mouse.
Figure 10B:
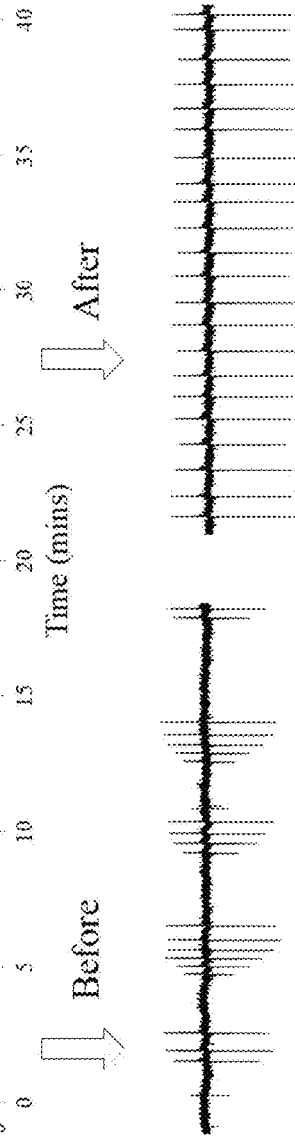
Figure 10C:
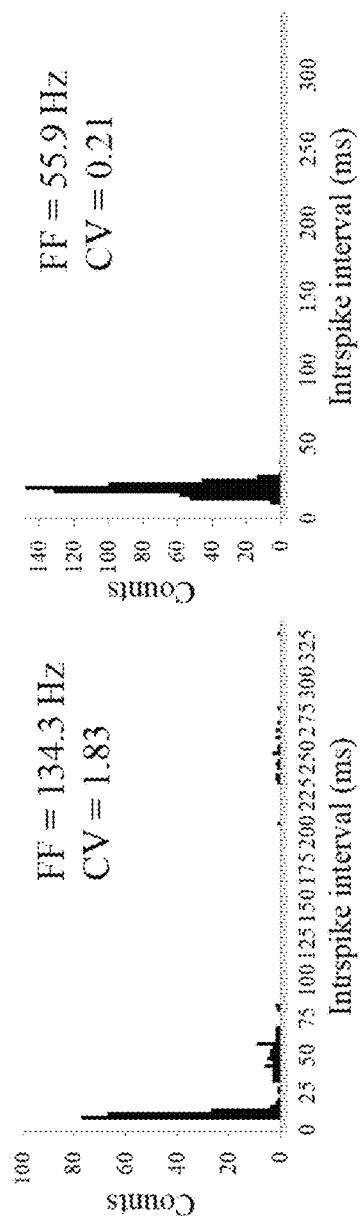

To investigate if positive allosteric modulators of K$_{Ca}$2 channels can rescue the abnormal firing of SCA2-58Q PCs, a series of experiments with acute cerebellar slices from 7-8-month-old SCA2-58Q mice was performed in the presence of the non-selective K$_{Ca}$2.x/K$_{Ca}$3.1 channel modulator CHZ (chlorzoxazone as a positive control) and the subtype-selective modulators 2o and 2q. Application of 50 μM CHZ converted bursting SCA2-58Q PC to tonic firing pattern (FIGS. 8A and B), and also significantly decreased the firing frequency of the cell and improved the regularity of PC activity (FIG. 8C). The ISI distribution before and after CHZ application, obtained from 10-s fragments of the recording was analyzed (FIG. 8C). The ISI distribution before the exposure to CHZ shows two peaks, whereas the ISI distribution after CHZ application trends to the normal distribution. Application of 10 µM 2o converted bursting SCA2-58Q PC to tonic firing pattern too (FIGS. 9A and B), and significantly decreased the firing frequency of the cell and also improved the regularity of PC activity (FIG. 9C). The ISI distribution before and after 2o application, obtained from 10-s fragments of the recording was also analyzed (FIG. 9C). The ISI distribution before the exposure to 2o shows two peaks, whereas the ISI distribution after 2o application trends to the normal distribution. Application of 10 µM 2q converted bursting SCA2-58Q PC to tonic firing pattern too (FIGS. 10A and B), and significantly decreased the firing frequency of the cell and also improved the regularity of PC activity a (FIG. 10C). However, in 8 minutes after 2q application, the activity of the cell switched to the silent mode (FIG. 10A). This may be explained by the higher potency of 2q compared to 2o. Thus, with a similar concentration of compounds, 2q causes more dramatic effect than 2o and limits the firing activity of PCs. The ISI distribution before and after 2q application, obtained from 10-s fragments of the recording was also analyzed (FIG. 10A). The ISI distribution before the exposure to 2q shows few peaks, whereas the ISI distribution after 2q application trends to the normal distribution. In sum, these experiments suggested that activation of $K_{Ca}2$ channels restored tonic firing of PC cells in aging SCA2 mice. Thus, the application of positive allosteric modulators of $K_{Ca}2$ channels results in a reliable increase in regularity of SCA2-58Q PC firing pattern and hereby may have a potential therapeutic effect for SCA treatment.

The present disclosure demonstrates that CyPPA analogs are useful for subtype-selective positive modulation of $K_{Ca}2.2a/K_{Ca}2.3$ channels. Replacing the cyclohexane ring with more hydrophobic disubstituted phenyl groups improved the potency of the compounds on potentiating the $K_{Ca}2.2a$ channel, while retaining their subtype-selectivity. Newly developed compounds were able to normalize abnormal firing of PCs in cerebellar slices from SCA2 mouse model, demonstrating the therapeutic potential of these compounds for treating symptoms of ataxia.

Experimental Methods

Trans-4-aminocyclohexanol, 97% (Chem Block), 4-nitrocyclohexan-1-amine hydrochloride salt 95% (Chem Space), trans-4-methoxy-cyclohexaylamine 97% (J&W Pharmlab), 4-nitroaniline 95% (aa Blocks), 4-aminothiophenol, 97% (Aldrich), 4-fluorocyclohexan-1-amine hydrochloride>97% (Pharma Block Sciences), 4-aminocyclohexyl methanol, 95% (Enamine), trans-1,4-diaminocyclohexane, >98% (aa block), 4-chloro-2-fluoroaniline 99% (Acros organic), 3-chloro-4-fluoroaniline, 95%, 2-chloro-5-fluoroaniline, 95%, 5-chloro-2-fluoroaniline, 95%, 4-trifluoromethyl)aniline, 3-chloro-4-trifluoromethyl)aniline (95%), 5-chloro-4-trifluoromethyl)aniline (95%), 3-chloroaniline (95%), 2,3-difluoroaniline, 2,5-difluoroaniline (95%) (aa block) (Aldrich), 4-chloro-6-methyl-2-(2-methyl-1,3-Oxazol-4-yl) pyrimidine (95%) (Chem Space), 4-chloro-2-(3,5-dimethyl-1H-pyrazol-1-yl)-6-methylpyrimidine (95%) (Chem Space), 3-chloro-6-hydrazinyl-4-methylpyridazine, (95%) (Ambeed), 4-chloro-6-(3,5-dimethyl)-1H-pyrazol-1-yl) (95%) (Alalab), anhydrous N,N-dimethylformamide (DMF) (99.8%) (Sigma-Aldrich), dichloromethane (DCM), ethyl acetate (Fisher), acetonitrile HPLC grade (Fisher Chemical) were purchased from the commercial vendors. CyPPA was purchased from Alomone Labs. CyPPA was dissolved in DMSO to make stock solution of 100 mM. The stock solution was then diluted in bath solution to the final concentrations for patch-clamp recordings. All prepared compounds were purified using flash chromatography followed by reverse phase HPLC purification after using Gemini 10 mm C18 110A, LC column phenomenex, 250× 21.2 mm, at flow rate 7 ml/min. All compounds are >95% pure by HPLC analysis.

The chemical structures of final products were characterized by nuclear magnetic resonance spectrometry 1D) measured on a Bruker NMR spectrometer (400 MHz). The chemical shifts were reported in parts per millions (ppm). The compounds' molecular weights were confirmed by a high-resolution mass spectroscopy time-of-flight electrospray mass spectrometer.

General procedures for the synthesis of compounds 2a-j. 4-Chloro-2-(3,5-dimethyl-1H-pyrazol-1-yl)-6-methylpyrimidine (1a, 0.23 mmol, 51 mg) was dissolved in 2 mL of anhydrous N,N-dimethylformamide (DMF) and N,N-diisopropylethylamine (DIPEA) (3 mmol, 348 µL) was added to the solution. Then, the proper-amine was dissolved in a few mL of DMF and added dropwise over 20 min to the solution containing compound 1a, with stirring at room temperature for 36-48 h. The progress of the reactions was monitored by TLC. After completion of the reactions, the solvent was evaporated under reduced pressure, and the crude products were purified by flash chromatography using dichloromethane (DCM), and ethyl acetate at gradient 2-50%.

4-((2-(3,5-Dimethyl-1H-pyrazol-1-yl)-6-methylpyrimidin-4-yl)amino)cyclohexan-1-ol (2a). Compound 2a was prepared by reaction of compound 1a with 4-aminocyclohexan-1-ol (0.25 mmol, 28.8 mg) as described in general procedure. Yield 82%, as white powder. $^1$H NMR (400 MHz, DMSO-$d_6$) δ: 1.11-1.37 and 1.77-1.96 (m, 8H, 4 CH$_2$'s of cyclohexane ring), 2.15 (s, 3H, CH$_3$-3 of pyrazole ring), 2.20 (s, 3H, CH$_{3-6}$ of the pyrimidine ring), 2.64-2.72 (m, 1H, CH—NH of cyclohexane ring), 3.18 (s, 3H, CH$_3$ of pyrazole ring), 3.64-3.83 (m, 1H, CHOH), 4.56 (d, J=4.4 Hz, 1H, OH), 6.02 (s, 1H, H-4 of the pyrazole ring), 6.15 (s, 1H, H-5 of the pyrimidine ring), 7.38 (d, J=6.8 Hz, 1H, NH). $^{13}$C NMR (101 MHz, DMSO) δ 164.21, 162.69, 156.59, 148.00, 141.02, 108.66, 101.17, 68.18, 48.55, 33.99, 30.23, 23.40, 14.40, 13.43. HR-MS (ESI-qTOF) (m/z) [C$_{16}$H$_{23}$N$_5$O]: calcd 301.1903, found 302.76100 [M+H]$^+$, 324.5613 [M+Na]$^+$.

N$^1$-(2-(3,5-Dimethyl-1H-pyrazol-1-yl)-6-methylpyrimidin-4-yl)cyclohexane-1,4-diamine (2b). Compound 2b was prepared by reaction of compound 1a (0.23 mmol, 51 mg) and cyclohexane-1,4-diamine (0.15 mmol, 17.126 mg) Yield 64%, white powder. $^1$H NMR (400-MHz, DMSO-$d_6$) δ: 1.36-1.45 (m, 4H, C2 & CH$_2$-6 of the cyclohexyl ring), 1.91-2.10 (m, 4H, 3-3-CH$_2$ and 5-CH$_2$-5 of the cyclohexyl ring), 2.26 (s, 3H, 3-CH$_3$ of pyrazole ring), 2.36 (s, 3H, 6-CH$_3$ of the pyrimidine ring), 2.60-2.72 (m, 2H, C1-H and H-4 of the cyclohexyl ring), 3.17 (s, 3H, CH$_3$= of pyrazole ring), 3.72-3.91 (br, 2H, NH$_2$), 6.28 (s, 1H, H-4 of the pyrazole ring), 6.33 (s, 1H, C5-H of pyrimidine ring), 7.96-8.01 (br, 1H, NH). $^{13}$C NMR (101 MHz, DMSO-$d_6$) δ: 167.586, 162.04, 158.01, 151.49, 143.03, 111.40, 101.27, 49.21, 48.29, 29.39, 28.29, 20.41, 14.53, 13.42. HR-MS (ESI-qTOF) (m/z) [C$_{16}$H$_{24}$N$_6$]: calcd 300.2062, found, 301.94 30 [M+H]$^+$, 323.7408 [M+Na]$^+$.

(4-((2-(3,5-Dimethyl-1H-pyrazol-1-yl)-6-methylpyrimidin-4-yl)amino)cyclohexyl) methanol (2c). Compound 2c was prepared by reaction of compound 1a (0.23 mmol, 51 mg) and (4-aminocyclohexyl) methanol (0.25 mmol, 32.28 mg), as described in the general procedure. Yield 79%, white powder. $^1$H NMR (400 MHz, DMSO-$d_6$) δ: 1.27-1.44 (m, 5H, 2 $CH_2$ of cyclohexane ring, and CH—$CH_2$OH), 1.71-1.83 (m, 4H, 2-$CH_2$ of the cyclohexane ring), 2.15 (s, 3H, 3-$CH_3$ of pyrazole ring), 2.21 (s, 3H, 6-$CH_3$ of the pyrimidine ring), 2.60-2.73 (m, 1H, CH—NH of cyclohexane ring), 3.06 (s, 3H, $CH_3$-5 of pyrazole ring), 3.52 (d, 2H, J=6 Hz, $CH_2$OH), 4.42 (t, 1H, J=5.2, OH), 6.02 (s, 1H, H-4 of the pyrazole ring), 6.15 (s, 1H, H-5 of the pyrimidine ring), 7.40 (d, 1H, J=7.6 Hz, NH). $^{13}$C NMR (101 MHz, DMSO) δ 164.59, 160.47, 157.05, 148.44, 141.46, 109.07, 101.59, 66.66, 49.88, 42.26, 32.39, 24.59, 23.83, 14.85, 13.88. HR-MS (ESI-qTOF) (m/z) [$C_{17}H_{25}N_5O$]: calcd 315.2059, found 316.6403 [M+H]$^+$.

2-(3,5-Dimethyl-1H-pyrazol-1-yl)-N-(4-methoxycyclohexyl)-6-methylpyrimidin-4-amine (2d). Compound 2d was prepared by the reaction of compound 1a (0.23 mmol, 51 mg) and 4-methoxycyclohexan-1-amine (0.25 mmol, 32.28 mg). Yield (81%), white powder. $^1$H NMR (400 MHz, DMSO-$d_6$) δ: 1.25-1.38, and 2.10-2.18 (m, 8H, 4 $CH_2$'s of the cyclohexane ring), 2.21 (s, 3H, 3-$CH_3$ of pyrazole ring), 2.29 (s, 1H, 6-$CH_3$ of the pyrimidine ring), 2.59-2.71 (m, 1H, CH—NH), 3.02 (s, 3H, 5-$CH_3$ of pyrazole ring), 3.16-3.23 (m, 1H, CHO$CH_3$), 3.34 (s, 3H, O$CH_3$), 6.06 (s, 1H, H-4 of the pyrazole ring), 6.19 (s, 1H, H-5 of the pyrimidine ring) 7.40 (d, J=7.6 Hz, 1H, NH). $^{13}$C NMR (101 MHz, DMSO-$d_6$) δ: 162.62, 160.03, 156.60, 148.00, 141.01, 108.64, 101.15, 80.02, 66.21, 49.44, 31.95, 28.21, 23.41, 14.401, 13.43. HR-MS (ESI-qTOF) (m/z) [$C_{17}H_{25}N_5O$]: calcd 315.2059, found 316.3240 [M+H].

2-(3,5-Dimethyl-1H-pyrazol-1-yl)-N-(4-fluorocyclohexyl)-6-methylpyrimidin-4-amine (2e). Compound 2e was prepared by the reaction of compound 1a (0.23 mmol, 51 mg) and 4-fluorocyclohexan-1-amine (0.25 mmol, 29.28 mg). Yield (77%), white powder. $^1$H NMR (400 MHz, MeOD) δ: 1.36-1.47 and 1.66-1.77, 1.92-2.01 (m, 8H, 4 $CH_2$'s of the cyclohexane ring), 2.19 (s, 3H, 3-$CH_3$ of pyrazole ring), 2.34 (s, 3H, 6-$CH_3$ of the pyrimidine ring), 2.61-2.71 (m, 1H, CH—NH), 3.10 (s, 3H, 5-$CH_3$ of pyrazole ring), 3.21-3.30 (m, 1H, H-4), 6.08 (s, 1H, H-4 of the pyrazole ring), 6.28 (s, 1H, H-5 of the pyrimidine ring), 7.55 (d, J=6.4 Hz, 1H, NH). $^{13}$C NMR (101 MHz, MeOD) δ 167.22, 160.07, 156.64, 148.04, 141.05, 108.67, 101.19, 90.13, 49.48, 31.99, 28.24, 23.45, 14.45, 13.47. HR-MS (ESI-qTOF) (m/z) [$C_{16}H_{22}FN_5$]: calcd 303.1859, found 304.3240 [M+H]$^+$.

2-(3,5-Dimethyl-1H-pyrazol-1-yl)-6-methyl-N-(4-nitrocyclohexyl)pyrimidin-4-amine (2f). Compound 2f was prepared by the reaction of compound 1a (0.23 mmol, 51 mg) and 4-nitrocyclohexan-1-amine (0.25 mmol, 36.02 mg). Yield (77%), white powder. $^1$H NMR (400 MHz, MeOD) δ: 1.37-1.47 and 1.95-2.05, 2.14-2.18 (m, 6H, $CH_2$ cyclohexane ring), 2.24 (s, 3H, 3-$CH_3$ of pyrazole ring), 2.36 (dd, 2H, J=5.2 and 4.8 Hz, cyclohexane ring), 2.56 (s, 3H, 6-$CH_3$ of the pyrimidine ring), 2.70-2.79 (m, 1H, CH—NH), 3.17 (s, 3H, 5-$CH_3$ of pyrazole ring), 3.78-3.86 (m, 1H, CH—$NO_2$ of cyclohexane ring), 5.95 (s, 1H, H-4 of the pyrazole ring), 6.56 (s, 1H, H-5 of the pyrimidine ring), 7.74 (d, J=6.4 Hz, 1H, NH). $^{13}$C NMR (101 MHz, DMSO) δ 170.35, 161.92, 155.91, 148.38, 141.06, 108.35, 99.89, 87.85, 54.69, 29.65, 24.15, 23.79, 13.52, 13.30. HR-MS (ESI-qTOF) (m/z) [$C_{16}H_{22}N_6O_2$]: calcd, 330.1804, found 331.3850 [M+H]$^+$.

2-(3,5-Dimethyl-1H-pyrazol-1-yl)-6-methyl-N-(4-nitrophenethyl)pyrimidin-4-amine (2g). Compound 2g was prepared by the reaction of compound 1a (0.23 mmol, 51 mg) and 2-(4-nitrophenyl)ethan-1-amine (0.25 mmol, 41.52 mg). Yield (72%), yellowish powder. $^1$H NMR (400 MHz, DMSO-d6) δ: 2.16 (s, 3H, 3-$CH_3$ of pyrazole ring), 2.26 (s, 1H, 6-$CH_3$ of the pyrimidine ring), 2.90 (t, J=7.2, Hz, 2H, NH$CH_2CH_2$), 3.09 (s, 3H, $CH_3$ of the pyrazole ring) 3.37 (t, 2H, J=7.2 Hz, NH$CH_2CH_2$), 6.00 (s, 1H, H-4 of the pyrazole ring), 6.51 (s, 1H, H-5 of the pyrimidine ring), 7.46 (d, 2H, J=8.0 Hz, C—H phenyl ring), 7.60-7.71 (br., s, 1H, NH), 8.09 (d, 2H, J=8.00 Hz, C—H phenyl ring). $^{13}$C NMR (101 MHz, DMSO-D6) δ $^{13}$C NMR (101 MHz, DMSO-d6) δ 167.62, 160.22, 156.65, 149.12, 145.90, 145.39, 141.07, 130.47, 124.81, 108.71, 101.22, 45.90, 34.05, 24.52, 15.28, 13.49. HR-MS (ESI-qTOF) (m/z) [$C_{18}H_{20}N_6O_2$]: calcd, 352.1648, found 353.3240 [M+H]$^+$.

3-(4-Cyanophenyl)-2-((2-(3,5-dimethyl-1H-pyrazol-1-yl)-6-methylpyrimidin-4-yl)amino)propanoic acid (2h). Compound 2h was prepared by the reaction of compound 1a (0.23 mmol, 51 mg) and 2-amino-3-(4-cyanophenyl)propanoic acid (0.23 mmol, 43.72 mg)). Yield (54%), yellowish powder. $^1$H NMR (400 MHz, CDCl$_3$) δ: 2.32 (s, 3H, 3-$CH_3$ of pyrazole ring), 2.47 (s, 1H, 6-$CH_3$ of the pyrimidine ring), 3.11 (s, 3H, 5-$CH_3$ of the pyrazole ring), 3.17 (dd, J=4.4, 4.4 Hz, 1H, β-$CH_2$), 3.43 (dd, 1H, J=4.0, 5.2 Hz, β-$CH_2$), 3.91 (t, J=3.6 Hz, 1H, α-CH), 6.07 (s, 1H, H-4 of the pyrazole ring), 6.46 (s, 1H, H-5 of the pyrimidine ring), 7.06 (d, 2H, J=8.0 Hz, C—H phenyl ring), 7.43 (d, 2H, J=8.0 Hz, C—H phenyl ring), 7.70 (d, 1H, J=7.6 Hz, NH), 11.19 (br, s, 1H, COOH). HR-MS (ESI-qTOF) (m/z) [$C_{20}H_{20}N_6O_2$]: calcd, 376.1648, found 377. 1682 [M+H]$^+$.

(2-(3,5-Dimethyl-1H-pyrazol-1-yl)-6-methylpyrimidin-4-yl)tyrosine(2i). Compound 2i was prepared by the reaction of compound 1a (0.23 mmol, 51 mg) and 2-amino-3-(4-hydroxyphenyl)propanoic acid (0.25 mmol, 49.28 mg). Yield (54%), yellowish powder. $^1$H NMR (400 MHz, DMSO) δ: 2.18 (s, 3H, 3-$CH_3$ of pyrazole ring), 2.34 (s, 1H, 6-$CH_3$ of the pyrimidine ring), 3.05 (s, 3H, 5-$CH_3$ of the pyrazole ring), 3.16 (dd, J=4.4, 4.4 Hz, 1H, β-$CH_2$), 3.42 (dd, 1H, J=4.4, 4.4 Hz, β-$CH_2$), 3.91 (t, J=7.6 Hz, 1H, α-CH), 6.09 (s, 1H, H-4 of the pyrazole ring), 6.50 (s, 1H, H-5 of the pyrimidine ring), 6.67 (d, 2H, J=7.2 Hz, C—H phenyl ring), 7.06 (d, 2H, J=7.2 Hz, C—H phenyl ring), 7.92 (d, 1H, J=7.6 Hz, NH), 11.10 (br, s, 1H, COOH). HR-MS (ESI-qTOF) (m/z) [$C_{19}H_{21}N_5O_3$]: calcd 367.1644, found 368.1678 [M+H]$^+$.

3-(3,4-Difluorophenyl)-2-((2-(3,5-dimethyl-1H-pyrazol-1-yl)-6-methylpyrimidin-4-yl)amino)propanoic acid (2j). Compound 2j was prepared by the reaction of compound 1a (0.23 mmol, 51 mg) and 2-amino-3-(3,4-difluorophenyl)propanoic acid (0.23 mmol, 49.93 mg). Yield (32%), white powder. $^1$H NMR (400 MHz, CDCl$_3$) δ: 2.25 (s, 3H, 3-$CH_3$ of pyrazole ring), 2.44 (s, 1H, 6-$CH_3$ of the pyrimidine ring), 3.05 (s, 3H, 5-$CH_3$ of the pyrazole ring), 3.16 (dd, J=4.4, 4.4 Hz, 1H, β-$CH_2$), 3.50 (dd, 1H, J=4.4, 4.4 Hz, β-$CH_2$), 3.93 (t, 1H, J=7.6 Hz, α-CH), 5.98 (s, 1H, H-4 of the pyrazole ring), 6.55 (s, 1H, H-5 of the pyrimidine ring), 7.00-7.08 (m, 2H, C—H phenyl ring), 7.08 (dd, 1H, J=2.4, 2.4 Hz, C—H phenyl ring), 7.66 (dd, 1H, J=2.4, 2.4 Hz, C—H phenyl ring), 7.96 (br, s, 1H, NH). HR-MS (ESI-qTOF) (m/z) [$C_{19}H_{19}F_2N_5O_2$]: calcd 387.1507, found 388.1540 [M+H]$^+$.

General procedures for the synthesis of compounds 2k-w, 3a-, 4, 5a,b, 6a,b, and 7. Compound 1a, 1b, 1c, 1d, or 1e (0.23 mmol) was dissolved in 2 mL of anhydrous N,N-dimethylformamide (DMF), N,N-diisopropylethylamine (DIPEA) (3 mmol, 348 μL) was added to the solution. Then, 0.25 mmol of the proper aniline or heterocyclic amine dissolved in 3 mL of DMF was added dropwise over 20 min. with stirring under reflux at 95° C. for 36-48 h. The progress of the reactions was monitored by TLC. After completion of the reactions, the solvent was evaporated under reduced pressure, and the crude products were purified by flash chromatography using DCM, and ethyl acetate at gradient 0-50%.

4-((2-(3,5-Dimethyl-1H-pyrazol-1-yl)-6-methylpyrimidin-4-yl)amino)-benzenethiol (2k). Compound 2k was prepared by reaction of compound 1a (0.23 mmol, 51 mg) and 4-aminobenzenethiol (0.25 mmol, 31.25 mg). Yield (68%), yellow powder. $^1$H NMR (400 MHz, DMSO-$d_6$): δ 2.17 (s, 3H, 3-CH$_3$ of pyrazole ring), 2.27 (s, 3H, 6-CH$_3$ of the pyrimidine ring), 2.31 (s, 3H, 5-CH$_3$ of the pyrazole ring), 5.23 (s, 1H, SH), 5.88 (s, 1H, H-4 of the pyrazole ring), 6.43 (s, 1H, H-5 of the pyrimidine ring), 6.66 (d, 2H, J=8.4 Hz, H-2 & H-6 of the phenyl ring), 7.27 (d, 2H, J=8.8 Hz, H-3 and H-5 of the phenyl ring). $^{13}$C NMR (101 MHz, DMSO-$d_6$) δ 174.97, 167.60, 155.73, 151.06, 149.45, 142.00, 137.15, 114.92, 112.25, 109.54, 109.50, 23.689, 14.26, 13.41. HR-MS (ESI-qTOF) (m/z) [$C_{16}H_{17}N_5S$] calcd 311.1205, found 312.1303 [M+H]$^+$.

2-(3,5-Dimethyl-1H-pyrazol-1-yl)-6-methyl-N-(4-nitrophenyl)pyrimidin-4-amine (2l). Compound 2l was prepared by the reaction of compound 1a (0.23 mmol, 51 mg) and 4-nitroaniline (0.25 mmol, 32.53 mg at 130° C. Yield (66%), yellow powder). $^1$H NMR (400 MHz, DMSO-$d_6$) δ: 2.23 (s, 3H, 3-CH$_3$ of pyrazole ring), 2.42 (s, 3H, 6-CH$_3$ of the pyrimidine ring), 2.56 (s, 3H, CH$_3$-5 of the pyrazole ring), 6.13 (s, 1H, H-4 of the pyrazole ring), 6.70 (s, 1H, C5-H of the pyrimidine ring), 8.03 (d, 2H, J=8.8 Hz, H-2 and H-6 of the phenyl ring), 8.23 (d, 2H, J=9.2 Hz, H-3 and H-5 of the phenyl ring), 10.38-10.45 (s, br., 1H, NH). $^{13}$C NMR (101 MHz, DMSO-$d_6$) δ 167.00, 160.66, 156.03, 149.11, 146.34, 141.57, 125.08, 118.86, 109.28, 103.65, 2366, 14.45, 13.54. HR-MS (ESI-qTOF) (m/z) [$C_{16}H_{16}N_7O_2$]: calcd 324.1335, found 348.3758 [M+Na]$^+$.

N-(2,3-Difluorophenyl)-2-(3,5-dimethyl-1H-pyrazol-1-yl)-6-methyl-pyrimidin-4-amine (2m). Compound 2m was prepared by the reaction of compound 1a (0.23 mmol, 51 mg) and 2,3-difluoroaniline (0.25 mmol, 32.28 mg) Yield (47%), as a white powder. $^1$H NMR (400 MHz, CDCl$_3$) δ: 2.38 (s, 3H, CH$_3$-3 of pyrazole ring), 2.465 (s, 3H, CH$_3$-6 of the pyrimidine ring), 2.57 (s, 3H, 5-CH$_3$ of the pyrazole ring), 6.04 (s, 1H, H-4 of the pyrazole ring), 6.55 (s, 1H, H-5 of the pyrimidine ring), 7.00 (dd, 1H, J=8.0, 3.2 Hz, H-4 of the phenyl ring), 7.08 (dd, 1H, J=8.4, 3.2 Hz, H-6 of the phenyl ring), 7.41 (t, 1H, J=7.6 Hz, H-5 of the phenyl ring), 8.03 (s, 1H, NH). $^{13}$C NMR (101 MHz, CDCl$_3$) 162.62, 161.20, 160.12, 156.58, 152.97, 141.17, 140.59, 136.80, 131.02, 129.41, 118.48, 111.58, 108.73, 22.62, 15.12, 13.29. HR-MS (ESI-qTOF) (m/z) [$C_{16}H_{15}F_2N_5$]: calcd 315.1296, found 316.139984 [M+H]$^+$.

N-(2,5-Difluorophenyl)-2-(3,5-dimethyl-1H-pyrazol-1-yl)-6-methylpyrimidin-4-amine (2n). Compound 2n was prepared by reaction of compound 1a (0.23 mmol, 51 mg) and 2,5-difluoroaniline (0.25 mmol, 32.28 mg). Yield (55%), white powder. $^1$H NMR (400 MHz, CDCl$_3$) δ: 2.32 (s, 3H, 3-CH$_3$ of pyrazole ring), 2.47 (s, 3H, 6-CH$_3$ of the pyrimidine ring), 2.56 (s, 3H, 5-CH$_3$ of the pyrazole ring), 6.03 (s, 1H, H-4 of the pyrazole ring), 6.54 (s, 1H, H-5 of the pyrimidine ring), 6.84 (dt, 1H, J=8.0, 4.0 Hz, —H-4 of the phenyl ring), 7.09 (dt, 1H, J=9.6, 4.0 Hz, H-3 of the phenyl ring), 7.52-7.62 (br. m, 1H, H-6 of the phenyl ring), 8.07-8.19 (br. s, 1H, NH). $^{13}$C NMR (101 MHz, CDCl$_3$) δ 167.13, 162.71, 160.73, 159.88, 158.70, 157.66, 149.91, 147.52, 128.04, 115.07, 109.98, 108.06, 23.911, 17.02, 14.27. HR-MS (ESI-qTOF) (m/z) [$C_{16}H_{15}F_2N_5$]: calcd 315.1296, found 316.4337 [M+H]$^+$.

N-(3-Chloro-4-fluorophenyl)-2-(3,5-dimethyl-1H-pyrazol-1-yl)-6-methyl-pyrimidin-4-amine (2o). Compound 2o was prepared by the reaction of compound 1a (0.23 mmol, 51 mg) and 3-chloro-4-fluoroaniline (0.25 mmol, 36.39 mg). Yield (83%), white powder. $^1$H NMR (400 MHz, CDCl$_3$) δ: 2.30 (s, 3H, 3-CH$_3$ of pyrazole ring), 2.39 (s, 3H, 5-CH$_3$ of the pyrazole ring), 2.59 (s, 3H, 6-CH$_3$ of the pyrimidine ring), 5.99 (s, 1H, C4-H of the pyrazole ring), 6.31 (s, 1H, H-5 of the pyrimidine ring), 7.13 (s, 1H, H-2 of the phenyl ring), 7.15 (t, 1H, J=4.0 Hz, H-5), 7.20 (s, 1H, NH), 7.47 (dd, 1H, J=6.4, 2.0 Hz, C6-H of the phenyl ring). $^{13}$C NMR (101 MHz, CDCl$_3$) δ 168.01, 162.20, 156.99, 154.43, 151.03, 142.90, 134.77, 125.60, 123.16, 121.80, 117.15, 110.09, 99.75, 24.32, 15.45, 13.98. HR-MS (ESI-qTOF) (m/z) [$C_{16}H_{15}ClFN_5$]: calcd 331.1000, found 332.104126 [M+H]$^+$.

N-(4-Chloro-2-fluorophenyl)-2-(3,5-dimethyl-1H-pyrazol-1-yl)-6-methyl-pyrimidin-4-amine (2p). Compound 2p was prepared by the reaction of compound 1a (0.23 mmol, 51 mg) and 4-chloro-2-fluoroaniline (0.25 mmol, 36.39 mg). Yield (79%), white powder. $^1$H NMR (400 MHz, CDCl$_3$) δ: 2.23 (s, 3H, CH$_3$-3 of pyrazole ring), 2.45 (s, 3H, CH$_3$-5 of the pyrazole ring), 2.47 (s, 3H, CH$_3$-6 of the pyrimidine ring), 6.03 (s, 1H, H-4 of the pyrazole ring), 6.68 (s, 1H, H-5 of the pyrimidine ring), 7.05 (t, 1H, J=8.8 Hz, H-5 of the phenyl ring). 7.23 (td, 1H, J=6.0, 2.4 Hz, H-6 of the phenyl ring), 7.60 (dd, 1H, J=6.4, 2.4 Hz, H-3 of the phenyl ring), 10.14-10.57 (br, s, 1H, NH). $^{13}$C NMR (101 MHz, CDCl$_3$) δ 161.98, 157.06, 154.59, 153.45, 151.61, 143.95, 133.75, 125.35, 123.09, 120.99, 116.71, 112.39, 102.45, 20.81, 15.23, 13.44. HR-MS (ESI-qTOF) (m/z) [$C_{16}H_{15}ClFN_5$]: calcd 331.1000, found 332.108978 [M+H]$^+$.

N-(5-Chloro-2-fluorophenyl)-2-(3,5-dimethyl-1H-pyrazol-1-yl)-6-methylpyrimidin-4-amine (2q). Compound 2q was prepared by the reaction of compound 1a (0.23 mmol, 51 mg) and 5-chloro-2-fluoroaniline (0.25 mmol, 36.39 mg). Yield (72%), white powder. $^1$H NMR (400 MHz, CDCl$_3$) δ: 2.32 (s, 3H, CH$_3$-3 of pyrazole ring), 2.47 (s, 3H, CH$_3$-5 of the pyrazole ring), 2.59 (s, 3H, CH$_3$-6 of the pyrimidine ring), 6.02 (s, 1H, H-4 of the pyrazole ring), 6.48 (s, 1H, H-5 of the pyrimidine ring), 7.08 (d, J=8.0 Hz, 2H, H-4 and H-3 of the phenyl ring), 7.45-7.70 (br, s, 1H, NH), 7.91 (d, 1H, J=6.4 Hz, H-6 of the phenyl ring). $^{13}$C NMR (101 MHz, CDCl3) δ 164.90, 161.81, 154.53, 152.47, 151.94, 143.62, 129.56, 127.05, 125.98, 124.69, 117.09, 111.07, 101.80, 23.03, 15.13, 13.59. HR-MS (ESI-qTOF) (m/z) [$C_{16}H_{15}ClFN_5$]: calcd 331.1000, found 332.112122 [M+H]$^+$.

N-(2-Chloro-5-fluorophenyl)-2-(3,5-dimethyl-1H-pyrazol-1-yl)-6-methylpyrimidin-4-amine (2r). Compound 2r was prepared by the reaction of compound 1a (0.23 mmol, 51 mg) and 2-chloro-5-fluoroaniline (0.25 mmol, 36.39 mg). Yield (79%), white powder. $^1$H NMR (400 MHz, CDCl$_3$) δ: 2.29 (s, 3H, CH$_3$-3 of pyrazole ring), 2.45 (s, 3H, 5-CH$_3$ of the pyrazole ring), 2.54 (s, 3H, 6-CH$_3$ of the pyrimidine ring), 6.00 (s, 1H, H-4 of the pyrazole ring), 6.50 (s, 1H, H-5 of the pyrimidine ring), 7.05 (dd, 2H, J=8.4, 2.4 Hz, H-4 and H-6 of the phenyl ring), 7.85 (d, 1H, J=5.6 Hz, H-3 of the phenyl ring), 8.01-8.06 (br., s, 1H, NH). $^{13}$C NMR (101 MHz, CDCl$_3$) δ 166.64, 162.76, 161.46, 155.75, 151.41, 143.09, 129.47, 127.36, 125.11, 124.11, 116.66, 110.48, 101.59, 23.65, 15.20, 13.78. HR-MS (ESI-qTOF) (m/z) [[$C_{16}H_{15}ClFN_5$]]: calcd 331.1000. found 332.110931 [M+H]$^+$.

2-(3,5-Dimethyl-1H-pyrazol-1-yl)-6-methyl-N-(4-(trifluoromethyl)-phenyl)pyrimidin-4-amine (2s). Compound 2s was prepared by the reaction of compound 1a (0.23 mmol, 51 mg) and 4-(trifluoromethyl)aniline (0.25 mmol, 40.28 mg). Yield (74%), white powder. $^1$H NMR (400 MHz, CD$_2$Cl$_2$): δ 2.33 (s, 3H, 3-CH$_3$ of pyrazole ring), 2.47 (s, 3H, 6-CH$_3$ of the pyrimidine ring), 2.59 (s, 3H, 5-CH$_3$ of the pyrazole ring), 6.13 (s, 1H, H-4 of the pyrazole ring), 6.84 (s, 1H, H-5 of the pyrimidine ring), 7.56-7.65 (m, 4H, H-2, H-3, H-5, and H-6 of the phenyl ring), 10.18-10.50 (br s, 1H, NH). $^{13}$C NMR (101 MHz, CD$_2$Cl$_2$): δ 164.68, 162.38, 156.55, 152.83, 144.84, 141.42, 126.82, 125.50, 124.75, 122.74, 112.08, 102.71, 23.21, 15.47, 13.46. HR-MS (ESI-qTOF) (m/z) [C$_{17}$H$_{16}$F$_3$N$_5$]: calcd 347.1358, found 348.3704 [M+H]$^+$.

N-(3-Chloro-4-(trifluoromethyl)phenyl)-2-(3,5-dimethyl-1H-pyrazol-1-yl)-6-methyl-pyrimidin-4-amine (2t). Compound 2t was prepared by the reaction of compound 1a (0.23 mmol, 51 mg) and 3-chloro-4-(trifluoromethyl)aniline (0.25 mmol, 48.89 mg). Yield (77%), white powder. $^1$H NMR (400 MHz, CD$_2$Cl$_2$) δ: 2.24 (s, 3H, 3-CH$_3$ of pyrazole ring), 2.40 (s, 3H, 6-CH$_3$ of the pyrimidine ring), 2.56 (s, 3H, 5-CH$_3$ of the pyrazole ring), 6.05 (s, 1H, H-4 of the pyrazole ring), 6.64 (s, 1H, H-5 of the pyrimidine ring), 7.44 (d, 1H, J=8.4 Hz, H-6 of the phenyl ring). 7.55 (d, 1H, J=8.4 Hz, H-2 of the phenyl ring), 7.84 (s, 1H, C5-H of the phenyl ring), 8.11-8.56 (br s, 1H, NH). HR-MS (ESI-qTOF) (m/z) [C$_{17}$H$_{15}$ClF$_3$N$_5$]: calcd 381.0968, found 382.1094 [M+H]$^+$.

N-(3-Chloro-5-(trifluoromethyl)phenyl)-2-(3,5-dimethyl-1H-pyrazol-1-yl)-6-methylpyrimidin-4-amine (2u). Compound 2u was prepared by the reaction of compound 1a (0.23 mmol, 51 mg) and 3-chloro-5-(trifluoromethyl)aniline (0.25 mmol, 48.89 mg). Yield (75%), white powder. $^1$H NMR (400 MHz, CD$_2$Cl$_2$) δ: 2.25 (s, 3H, 3-CH$_3$ of pyrazole ring), 2.51 (s, 6H, 6-CH$_3$ of the pyrimidine ring and 5-CH$_3$ of the pyrazole ring), 6.10 (s, 1H, H-4 of the pyrazole ring), 6.80 (s, 1H, H-5 of the pyrimidine ring), 7.42 (s, 1H, H-6 of the phenyl ring). 7.69 (s, 1H, H-2 of the phenyl ring), 7.75 (s, 1H, H-5 of the phenyl ring), 10.00-10.39 (br., s, 1H, NH). 162.58, 158.77, 154.58, 151.40, 144.89, 139.48, 135.79, 132.88, 126.29, 124.96, 122.80, 118.11, 113.28, 103.83, 20.84, 15.44, 13.52. HR-MS (ESI-qTOF) (m/z) [C$_{17}$H$_{15}$ClF$_3$N$_5$]: calcd 381.0968, found 382.106476 [M+H]$^+$.

3-((2-(3,5-Dimethyl-1H-pyrazol-1-yl)-6-methylpyrimidin-4-yl)amino)-4-fluorobenzoic acid (2v). Compound 2v was prepared by the reaction of compound 1a (0.23 mmol, 51 mg) and 3-amino-4-fluorobenzoic acid (0.25 mmol, 38.78 mg). Yield (79%), white powder. $^1$H NMR (400 MHz, MeOD) δ: 2.28 (s, 3H, 3-CH$_3$ of pyrazole ring), 2.32 (s, 3H, 5-CH$_3$ of the pyrazole ring), 2.54 (s, 3H, 6-CH$_3$ of the pyrimidine ring), 6.17 (s, 1H, H-4 of the pyrazole ring), 6.66 (s, 1H, H-5 of the pyrimidine ring), 7.38 (t, 1H, J=8.8 Hz, H-5 of the phenyl ring), 8.0-8.04 (m, 1H, H-2 of the phenyl ring), 8.30 (dd, J=2.8, 7.6 Hz, 1H, NH). $^{13}$C NMR (101 MHz, MeOD) δ: 167.95, 164.66, 161.82, 159.28, 155.31, 152.47, 145.91, 131.32, 130.33, 128.95, 126.05, 117.67, 113.46, 102.97, 23.75, 15.07, 13.60. HR-MS (ESI-qTOF) (m/z) [C$_{17}$H$_{16}$FN$_5$O$_2$]: calcd 341.1288. found 342.1322 [M+H]$^+$.

N-(2-(3,5-Dimethyl-1H-pyrazol-1-yl)-6-methylpyrimidin-4-yl)-5,6-dimethoxy-1H-benzo[d]imidazol-2-amine (2w). Compound 2w was prepared by the reaction of compound 1a (0.23 mmol, 51 mg) and 5,6-dimethoxy-1H-benzo[d]imidazol-2-amine (0.25 mmol, 48.30 mg). Yield (75%), brown powder. $^1$H NMR (400 MHz, CDCl$_3$) δ: 2.30 (s, 3H, CH$_3$-3 of pyrazole ring), 2.39 (s, 3H, 6-CH$_3$ of the pyrimidine ring), 2.59 (s, 3H, 5-CH$_3$ of the pyrazole ring), 3.85 (s, 6H, 2OCH$_3$), 5.95 (s, 1H, H-4 of the pyrazole ring), 6.52 (s, 1H, H-5 of the pyrimidine ring), 7.15 (s, 2H, C—H of the benzoimidazol ring), 7.83 (s, 1H, NH). HR-MS (ESI-qTOF) (m/z) [C$_{19}$H$_{21}$N$_7$O$_2$]: calcd 379.1757, found 380.1990 [M+H]$^+$.

N$^1$-(3-Chlorophenyl)-6-(3,5-dimethyl-1H-pyrazol-1-yl)pyrimidine-2,4-diamine (3a). Compound 3a was prepared by reaction of compound 1b (4-chloro-6-(3,5-dimethyl-1H-pyrazol-1-yl)pyrimidin-2-amine, 0.23 mmol, 51.21 mg) with 3-chloroaniline (0.25 mmol, 31.89 mg). Yield (45%), white powder. $^1$H NMR (400 MHz, MeOD) δ 2.18 (s, 3H, 3-CH$_3$ of pyrazole ring), 2.50 (s, 3H, 5-CH$_3$ of pyrazole ring), 6.13 (s, 1H, H-5 of the pyrimidine ring), 6.33 (s, 1H, H-4 of the pyrazole ring), 7.08 (d, 1H, J=8.0 Hz, H-4 of phenyl ring), 7.26 (t, 1H, J=8.0 Hz, H-5 of phenyl ring), 7.44 (d, 1H, J=8.0 Hz, H-6 of the phenyl ring), 7.74 (s, 1H, H-2 of the phenyl ring). $^{13}$C NMR (101 MHz, MeOD) δ 171.78, 161.83, 160.06, 159.00, 153.81, 141.03, 135.77, 131.49, 124.92, 122.80, 121.01, 119.06, 112.81, 85.89, 14.54, 13.58. HR-MS (ESI-qTOF) (m/z) [C$_{15}$H$_{15}$ClN$_6$]: calcd 314.1047, found 315.113220 [M+H]$^+$.

N$^1$-(3-Chloro-4-fluorophenyl)-6-(3,5-dimethyl-1H-pyrazol-1-yl)pyrimidine-2,4-diamine (3b). Compound 3b was prepared by reaction of compound 1b (0.23 mmol, 51.21 mg) and 3-chloro-4-fluoroaniline (0.25 mmol, 36.39 mg). Yield (65%) as a white powder. $^1$H NMR (400 MHz, MeOD) δ 2.26 (s, 3H, 3-CH$_3$ of pyrazole ring), 2.57 (s, 3H, 5-CH$_3$ of pyrazole ring), 6.21 (s, 1H, H-5 of the pyrimidine ring), 6.38 (s, 1H, H-4 of the pyrazole ring), 7.24 (t, 1H, J=8.8 Hz, H-6 of phenyl ring), 7.53 (t, 1H, J=5.2 Hz, H-2 of phenyl ring), 7.91 (dd, 1H, J=6.8, 2.8 Hz, H-5 of phenyl ring). $^{13}$C NMR (101 MHz, MeOD) δ 163.47, 159.07, 157.61, 155.17, 153.77, 144.27, 136.69, 124.93, 123.10, 121.87, 118.03, 112.75, 85.66, 14.47, 13.58. HR-MS (ESI-qTOF) (m/z) [C$_{15}$H$_{14}$ClFN$_6$]: calcd 332.0953, found 333.104126 [M+H]$^+$.

N$^1$-(5-Chloro-2-fluorophenyl)-6-(3,5-dimethyl-1H-pyrazol-1-yl)pyrimidine-2,4-diamine (3c). Compound 3c was prepared by reaction of compound 1b (0.23 mmol, 51.21 mg) and 5-chloro-2-fluoroaniline (0.25 mmol, 36.39 mg). Yield (72%) as a white powder. $^1$H NMR (400 MHz, MeOD) δ 2.16 (s, 3H, 3-CH$_3$ of pyrazole ring), 2.58 (s, 3H, 5-CH$_3$ of pyrazole ring), 5.98 (s, 1H, H-5 of the pyrimidine ring), 6.48 (s, 1H, H-4 of the pyrazole ring), 6.85 (t, 1H, J=8.8 Hz, H-3 of phenyl ring), 7.38 (td, 1H, J=6.8, 2.8 Hz, H-4 of phenyl ring), 7.84 (dd, J=8.4 Hz, 1H, H-6 of phenyl ring). HR-MS (ESI-qTOF) (m/z) [C$_{15}$H$_{14}$ClFN$_6$]: calcd 332.09527 found 333.115021 [M+H]$^+$.

N$^1$-(4-Chloro-2-fluorophenyl)-6-(3,5-dimethyl-1H-pyrazol-1-yl)pyrimidine-2,4-diamine (3d). Compound 3d was prepared by reaction of compound 1b (0.23 mmol, 51.21 mg) and 4-chloro-2-fluoroaniline (0.25 mmol, 36.39 mg). Yield (54%) as a white powder. $^1$H NMR (400 MHz, MeOD) δ 2.23 (s, 3H, 3-CH$_3$ of pyrazole ring), 2.57 (s, 3H, CH$_3$ of pyrazole ring), 6.16 (s, 1H, H-5 of the pyrimidine ring), 6.47 (s, 1H, H-4 of the pyrazole ring), 7.22 (d, 1H, J=8.4 Hz, H-5 of phenyl ring), 7.28 (dd, 1H, J=10.8, 2.4 Hz, H-6 of phenyl ring), 7.98 (t, 1H, J=8.8 Hz, H-3 of phenyl ring). $^{13}$C NMR (101 MHz, MeOD) δ 163.76, 159.32, 157.71, 155.23, 153.70, 144.42, 132.05, 127.86, 126.19, 125.89, 117.71, 112.62, 85.38, 14.67, 13.39. HR-MS (ESI-qTOF) (m/z) [C$_{15}$H$_{14}$ClFN$_6$]: calcd 332.0952, found 334.1166 [M+H]$^+$.

N$^1$-(2-Chloro-5-fluorophenyl)-6-(3,5-dimethyl-1H-pyrazol-1-yl)pyrimidine-2,4-diamine (3e). Compound 3e was prepared by reaction of compound 1b (0.23 mmol, 51.21 mg) and 2-chloro-5-fluoroaniline (0.25 mmol, 36.39 mg).

Yield (51%) as a white powder. $^1$H NMR (400 MHz, MeOD) δ 2.15 (s, 3H, 3-CH$_3$ of pyrazole ring), 2.50 (s, 3H, 5-CH$_3$ of pyrazole ring), 6.03 (s, 1H, H-5 of the pyrimidine ring), 6.43 (s, 1H, H-4 of the pyrazole ring), 6.83 (td, 1H, J=9.2, 3.2 Hz, C4-H-4 of phenyl ring), 7.37 (td, 1H, J=9.2, 3.2 Hz, H-6 of phenyl ring), 7.82 (dd, 1H, J=10.4, 2.8 Hz, H-3 of phenyl ring). $^{13}$C NMR (101 MHz, MeOD) δ 164.02, 163.00, 162.47, 161.58, 152.97, 145.08, 144.15, 138.04, 131.94, 122.97, 113.29, 111.79, 86.23, 14.86, 13.59. HR-MS (ESI-qTOF) (m/z) [C$_{15}$H$_{14}$ClFN$_6$]: calcd 332.09527, found 334.116608 [M+H]$^+$.

N$^1$-(2,5-Difluorophenyl)-6-(3,5-dimethyl-1H-pyrazol-1-yl)pyrimidine-2,4-diamine (3f). Compound 3f was prepared by reaction of compound 1b (0.23 mmol, 51.21 mg) and 2,5-difluoroaniline (0.25 mmol, 32.28 mg). Yield (53%) as a white powder. $^1$H NMR (400 MHz, MeOD) δ 2.25 (s, 3H, 3-CH$_3$ of pyrazole ring), 2.58 (s, 3H, 5-CH$_3$ of pyrazole ring), 6.20 (s, 1H, H-5 of the pyrimidine ring), 6.57 (s, 1H, H-4 of the pyrazole ring), 6.88-6.93 (m, 1H, H-4 of phenyl ring), 7.17-7.23 (m, 1H, H-6 of phenyl ring), 8.03-8.08 (m, 1H, H-2 of phenyl ring). $^{13}$C NMR (101 MHz, MeOD) δ 163.92, 161.06, 159.55, 158.69, 153.67, 153.26, 150.86, 144.36, 130.96, 128.47, 117.25, 112.65, 85.94, 14.61, 13.58. HR-MS (ESI-qTOF) (m/z) [C$_{15}$H$_{14}$F$_2$N$_6$]: calcd 316.1248, found, 318.18147064 [M+2H]$^+$.

N$^1$-(3-Chloro-4-(trifluoromethyl)phenyl)-6-(3,5-dimethyl-1H-pyrazol-1-yl)pyrimidine-2,4-diamine (3g). Compound 3g was prepared by reaction of compound 1b (0.23 mmol, 51.21 mg) and 3-chloro-4-(trifluoromethyl)aniline (0.25 mmol, 48.89 mg. Yield (55%) as a white powder. $^1$H NMR (400 MHz, MeOD) δ 2.25 (s, 3H, 3-CH$_3$ of pyrazole ring), 2.58 (s, 3H, 5-CH$_3$ of pyrazole ring), 6.16 (s, 1H, H-5 of the pyrimidine ring), 6.43 (s, 1H, H-4 of the pyrazole ring), 6.88 (d, 1H, J=8.8 Hz, H-6 of phenyl ring), 7.76 (d, 1H, J=8.8 Hz, H-2 of phenyl ring), 8.08 (s, 1H, H-2 of phenyl ring). $^{13}$C NMR (101 MHz, MeOD) δ 163.93, 160.50, 154.24, 153.28, 145.03, 144.11, 133.54, 129.15, 128.60, 125.91, 123.17, 119.08, 112.22, 86.61, 14.50, 13.48. HR-MS (ESI-qTOF) (m/z) [C$_{16}$H$_{14}$ClF$_3$N$_6$]: calcd 382.0921, found 384.113861 [M+2H]$^+$.

N$^1$-(3-Chloro-4-fluorophenyl)-2-(3,5-dimethyl-1H-pyrazol-1-yl)pyrimidine-4,6-diamine (4). Compound 4 was prepared by reaction of compound 1c (4-chloro-(3,5-dimethyl-1H-pyrazol-1-yl)pyrimidine-6-amine, 0.23 mmol, 51.21 mg) and 3-chloro-4-fluoroaniline (0.25 mmol, 36.39 mg). Yield (73%), white powder. $^1$H NMR (400 MHz, MeOD) δ 2.27 (s, 3H, 3-CH$_3$ of pyrazole ring), 2.55 (s, 3H, 5-CH$_3$ of pyrazole ring), 5.74 (s, 1H, H-5 of the pyrimidine ring), 6.17 (s, 1H, H-4 of the pyrazole ring), 7.23-7.31 (m, 2H, H-5 and H-6 of phenyl ring), 7.63 (dd, 1H, J=6.4, 2.0 Hz, H-2 of the phenyl ring). $^{13}$C NMR (101 MHz, MeOD) δ 163.05, 157.91, 155.46, 153.88, 145.31, 136.75, 126.64, 124.48, 121.88, 118.17, 117.95, 112.59, 80.89, 15.42, 13.71. HR-MS (ESI-qTOF) (m/z) [C$_{15}$H$_{14}$ClFN$_6$]: calcd 332.0953, found 333.0991 [M+H]$^+$.

N-(5-Chloro-2-fluorophenyl)-6-methyl-2-(4-methyl-1H-imidazol-1-yl)pyrimidin-4-amine (5a). Compound 5a was prepared by reaction of compound 1d (4-chloro-6-methyl-2-(4-methyl-1H-imidazol-1-yl)pyrimidine, 0.24 mmol, 50 mg) and 5-chloro-2-fluoroaniline (0.25 mmol, 36.39 mg). Yield (71%), white powder. $^1$H NMR (400 MHz, MeOD) δ: 2.37 (s, 3H, 4-CH$_3$ of imidazole ring), 2.43 (s, 3H, 6-CH$_3$ of the pyrimidine ring), 6.70 (s, 1H, H-5 of the pyrimidine ring), 7.19 (t, 1H, J=7.6 Hz, H-4 of the phenyl ring), 7.22 (s, 1H, CH-6 of the phenyl ring), 7.84 (s, 1H, H-2 of imidazole ring), 7.95 (dd, 1H, J=6.8, 2.0 Hz, H-3 of the phenyl ring), 9.25 (s, 1H, H-5 of the imidazole ring). $^{13}$C NMR (101 MHz, MeOD) δ 169.38, 163.65, 156.35, 153.90, 135.05, 133.99, 130.19, 128.64, 126.56, 125.74, 118.23, 116.11, 105.76, 23.74, 10.61. HR-MS (ESI-qTOF) (m/z) [C$_{15}$H$_{13}$ClFN$_5$O$_3$]: calcd 317.0844, found 318.0922 [M+H]$^+$.

N-(3-Chloro-4-fluorophenyl)-6-methyl-2-(4-methyl-1H-imidazol-1-yl)pyrimidin-4-amine (5b). Compound 5b was prepared by reaction of compound 1d (0.24 mmol, 50 mg) and 3-chloro-4-fluoroaniline (0.25 mmol, 36.39 mg). Yield (76%), as white powder. $^1$H NMR (400 MHz, MeOD) δ: 2.37 (s, 3H, 4-CH$_3$ of imidazole ring), 2.41 (s, 3H, 6-CH$_3$ of the pyrimidine ring), 6.59 (s, 1H, H-5 of the pyrimidine ring), 7.25 (t, 1H, J=8.8 Hz, H-5 of the phenyl ring), 7.54 (dt, 1H, J=6.8, 2.8 Hz, C6-H of the phenyl ring,), 7.72 (dd, 1H, J=6.8, 2.4 Hz, C2-H of the phenyl ring), 7.90 (s, 1H, C2 of H-2 of imidazole ring), 9.29 (s, 1H, H-5 of the imidazole ring). $^{13}$C NMR (101 MHz, MeOD) δ 168.78, 163.34, 156.96, 154.53, 153.65, 137.09, 135.26, 134.13, 129.89, 124.02, 122.34, 117.99, 105.67, 23.69, 10.68. HR-MS (ESI-qTOF) (m/z) [C$_{15}$H$_{13}$ClFN$_5$]: calcd 317.0843; found, 318.0832.

N-(5-Chloro-2-fluorophenyl)-6-methyl-2-(2-methyloxazol-4-yl)pyrimidin-4-amine (6a). Compound 6a was prepared by reaction of compound 1e (4-(4-chloro-6-methylpyrimidin-2-yl)-2-methyloxazole, 0.24 mmol, 50.3 mg) and 2-chloro-5-fluoroaniline (0.25 mmol, 36.39 mg). Yield (74%), as a white powder. $^1$H NMR (400 MHz, MeOD) δ 2.39 (s, 3H, 6-CH$_3$ of the pyrimidine ring), 2.50 (s, 3H, 2-CH$_3$ of oxazole ring), 6.60 (s, 1H, H-5 of the pyrimidine ring), 7.03-7.07 (m, 1H, H-4 of the phenyl ring), 7.13 (dd, 1H, J=8.8, 2.0 Hz, H-3 of oxazole ring), 8.24 (s, 1H, H-5 of the oxazole ring), 8.37 (dd, 1H, J=6.8, 2.4 Hz, H-6 of the phenyl ring). $^{13}$C NMR (101 MHz, MeOD) δ 167.37, 164.10, 162.33, 159.30, 155.17, 152.74, 141.49, 130.17, 130.01, 124.53, 124.27, 117.55, 105.25, 23.63, 13.66. HR-MS (ESI-qTOF) (m/z) [C$_{15}$H$_{12}$ClFN$_4$O]: calcd 318.06837, found 319.07254 [M+H]$^+$.

N-(3-Chloro-4-fluorophenyl)-6-methyl-2-(2-methyloxazol-4-yl)pyrimidin-4-amine (6b). Compound 6b was prepared by reaction of compound 1e (3-chloro-6-(3,5-dimethyl-1H-pyrazol-1-yl)-4-methylpyridazine, 0.24 mmol, 50.3 mg) and 3-chloro-4-fluoroaniline (0.25 mmol, 36.39 mg). Yield (81%), white powder. $^1$H NMR (400 MHz, MeOD) δ 2.53 (s, 3H, 3-CH$_3$ of the pyrimidine ring), 2.57 (s, 3H, 2-CH$_3$ of oxazole ring), 6.68 (s, 1H, H-5 of the pyrimidine ring), 7.32 (t, 1H, J=8.8 Hz, H-5 of the phenyl ring), 7.53-7.57 (m, 1H, H-6 of the phenyl ring), 7.79 (dd, 1H, J=6.4, 2.4 Hz, H-2 of the phenyl ring), 8.61 (s, 1H, H-5 of the oxazole ring), 9.29 (s, 1H, NH). $^{13}$C NMR (101 MHz, MeOD) δ 165.15, 163.10, 158.17, 155.78, 155.09, 145.20, 135.83, 135.41, 125.67, 123.94, 122.17, 118.30, 112.68, 105.42, 19.51, 13.60. HR-MS (ESI-qTOF) (m/z) [C$_{15}$H$_{12}$ClFN$_4$O]: calcd 318.0683, found 319.0725 [M+H]$^+$.

N-(3-Chloro-4-fluorophenyl)-6-(3,5-dimethyl-1H-pyrazol-1-yl)-4-methylpyridazin-3-amine. Compound 7 was prepared by the reaction of compound 1f (0.23 mmol, 51.21 mg) and 3-chloro-4-fluoroaniline (0.25 mmol, 36.39 mg). Yield (65%), white powder. $^1$H NMR (400 MHz, CDCl$_3$) δ: 2.33 (s, 3H, CH$_3$ 3-CH$_3$ of pyrazole ring), 2.48 (s, 3H, 4-CH$_3$ of the piperazine ring), 2.58 (s, 3H, 5-CH$_3$ of the pyrazole ring), 6.07 (s, 1H, H-4 of the pyrazole ring), 6.67 (s, 1H, H-3 at the piperazine ring), 7.13 (t, 1H, J=8.8 Hz, H-5 of the phenyl ring), 7.26 (d, 1H, J=10 Hz, H-6 of the phenyl ring), 7.60 (dd, 1H, J=6.4, 2.0 Hz, C2-H of the phenyl ring), 9.84-10.10 (br s, 1H, NH). $^{13}$C NMR (101 MHz, CDCl$_3$) δ 161.99, 157.02, 154.55, 153.27, 152.55, 143.75, 134.11, 125.26, 123.10, 121.22, 117.14, 111.65, 101.72, 22.16, 15.31, 13.58. HR-MS (ESI-qTOF) (m/z) [$C_{16}H_{15}ClFN_5$]: calcd 331.1000, found 332.103271 [M+H]$^+$.

Electrophysiology

The effect of newly synthesized compounds on the $K_{Ca}2.x/K_{Ca}3.1$ channels was investigated as previously described (Nam, Y. W.; et al, *Acta Physiol (Oxf)* 2020, e13552; Nam, Y. W.; et al. *Scientific reports* 2018, 8 (1), 10749). Briefly, the rat $K_{Ca}2.2a$, human $K_{Ca}2.1$, human $K_{Ca}2.3$ or human $K_{Ca}3.1$ channels cDNA constructs were either generated in-house or through molecular cloning services (Genscript). The channel cDNAs, along with CaM and GFP, at a ratio of 7:4:2 (ORF ratios), were transfected into HEK293 cells by the calcium-phosphate method. $K_{Ca}$ currents were recorded 1-2 days after transfection, with an Axon200B amplifier (Molecular Devices) at room temperature. The resistance of the patch electrodes ranged from 3-5 MΩ. The pipette solution contained (in mM): 140 KCl, 10 Hepes (pH 7.4), 1 $MgSO_4$. The bath solution containing (in mM): 140 KCl, 10 Hepes (pH 7.2), 1 EGTA, 0.1 Dibromo-BAPTA, and 1 HEDTA was mixed with $Ca^{2+}$ to obtain the desired free $Ca^{2+}$ concentrations, calculated using the software by Chris Patton of Stanford University (https://somapp.ucdmc.ucdavis.edu/pharmacology/bers/maxchelator/webmaxc/webmaxcS.htm). The $Ca^{2+}$ concentrations were verified using a $Ca^{2+}$ calibration buffer kit (Thermo Fisher Scientific). Briefly, a standard curve was generated using the $Ca^{2+}$ buffers from the kit and a fluorescence $Ca^{2+}$ indicator. Then, the $Ca^{2+}$ concentrations of the bath solution were determined through interpolation on the standard curve.

High resistance seals (>1 GΩ) were formed before inside-out patches were obtained. The seal resistance of inside-out patches was >1 GΩ, when the intracellular face was initially exposed to a zero-$Ca^{2+}$ bath solution. Currents were recorded by repetitive 1-s-voltage ramps from −100 mV to +100 mV from a holding potential of 0 mV. The currents were filtered at 2 kHz and digitized at a sampling frequency of 10 kHz. At the end of experiment, the integrity of the patch was examined by switching the bath solution back to the zero-$Ca^{2+}$ buffer. Data from patches, which maintained the seal resistance (>1 GΩ) after solution changes, were used for further analysis.

To measure the effect of CyPPA (Alomone Labs) and newly synthesized compounds, the intracellular face was exposed to bath solutions with 0.15 μM $Ca^{2+}$. One minute after switching of bath solutions, ten sweeps with a 1-s interval were recorded at a series of concentrations of compound in the presence of 0.15 μM $Ca^{2+}$. The maximal $K_{Ca}2.x/K_{Ca}3.1$ current in response to 10 μM $Ca^{2+}$ was then recorded.

Data and Statistical Analysis

Patch-clamp recordings were analyzed using Clampfit 10.5 (Molecular Devices LLC) and concentration-response curves were analyzed in GraphPad Prism 9.0.2 (GraphPad Software Inc.). To construct the concentration-dependent potentiation of channel activities by compound, the current amplitudes at −90 mV in response to various concentrations of the compound were normalized to that obtained at a maximal concentration of compound. The normalized currents were plotted as a function of the concentrations of the compound. $EC_{50}$ values and Hill coefficients were determined by fitting the data points to a standard concentration-response curve ($Y=100/(1+(X/EC50)^\wedge-Hill)$). To assess the efficacy of compound, the current amplitudes obtained at the maximal concentration of the compound were normalized to the maximal $K_{Ca}2.x/K_{Ca}3.1$ current in response to 10 μM $Ca^{2+}$. Concentration-response curves were acquired from multiple patches for each data set. Each curve was fitted individually, which yielded the $EC_{50}$ value for that curve. $EC_{50}$ values are shown as mean±SEM obtained from multiple patches, and the number of patches is indicated by n.

The Student's t-test was used for data comparison if there were only two groups. One-way ANOVA and Tukey's post hoc tests were used for data comparison of three or more groups. Post hoc tests were carried out only if F was significant and there was no variance in homogeneity.

Mice Breeding and Genotyping

Transgenic SCA2-58Q mice and their wild type (WT) littermates were used in these experiments. SCA2-58Q mice were kindly provided to us by Dr. Stefan Pulst (University of Utah) and were crossed to the FVB background strain. Hemizygous male SCA2-58Q mice were crossed with the WT female mice to generate mixed litters. The genotyping was done via PCR for ATXN2 transgene. The volume of one PCR sample was 25 μl. The PCR mix per one sample contained: 2.5 μl 10× buffer for Taq polymerase, 0.5 μl 10 mM dNTP, 1.5 μl 25 mM $MgCl_2$, 0.125 μl 20 μM primers (forward and reverse), 0.25 μl Taq polymerase, 2 μl DNA, and 18 μl $dH_2O$. For forward and reverse primer sequences, see e.g., Egorova et al., Cell Calcium, 2021 January; 93: 102319. The PCR product has 232 bp. Mice were housed in groups of two to six in one cage in the vivarium. The temperature was kept 22-24° C. including 12 daylight hours. The animals had access to standard food and water ad libitum. All procedures were approved by the Bioethics Committee of the Peter the Great St. Petersburg Polytechnic University at St. Petersburg, Russia, and followed the principles of the European convention (Strasbourg, 1986) and the Declaration of International medical association about humane treatment of animals (Helsinki, 1996).

Cerebellar Slice Recordings of Spontaneous PC Activity in SCA2-58Q Mice

Recordings of spontaneous PC activity from WT and SCA2-58Q mice at 7-8 months of age were performed. Briefly, the mice were anesthetized with 2,000 mg/kg urethane and transcardially perfused with ice-cold aCSF containing 85 mM NaCl, 24 mM $NaHCO_3$, 25 mM glucose, 2.5 mM KCl, 0.5 mM $CaCl_2$, 4 mM $MgCl_2$, 1 mM $NaH_2PO_4$, and 75 mM sucrose. Solutions were equilibrated with carbogen (95% $O_2$/5% $CO_2$). Next, the cerebellum was dissected and 300 μm thick sagittal slices were cut with a VT1200S vibratome (Leica). Slices were recovering in aCSF containing 119 mM NaCl, 26 mM $NaHCO_3$, 11 mM glucose, 2.5 mM KCl, 2.5 mM $CaCl_2$, 1.3 mM $MgCl_2$, and 1 mM $NaH_2PO_4$ at 35° C. for 30-40 min and then transferred to the room temperature before recordings started. The external bath solution used for the recording was the same as the recovery aCSF, but also contained 100 μM picrotoxin (PTX) and 10 μM 6,7-dinitroquinoxaline-2,3-dione (DNQX), equilibrated with carbogen. All recordings were made within 5-6 hours after cerebellum was dissected. The recording chamber was heated to 35° C. using TC-324C automatic temperature controller (Warner Instruments). Loose-patch recordings were made to evaluate the spontaneous activity of cerebellar PCs. Briefly, 1-3 MΩ glass pipettes were filled with the internal solution containing 140 mM NaCl buffered with 10 mM HEPES pH 7.3 and held at 0 mV. A loose patch (<100 MΩ) configuration was established at the PC soma at the axon hillock area. Spontaneous action potential currents were recorded for 5-60 min from each cell using Axon Multiclamp 700B amplifier (Molecular Devices). The 10 min recordings were analyzed for tonic or burst firing. Cells were characterized as firing tonically if they fired repetitive nonhalting spike trains for 10 min. A cell was characterized as bursting if it had more than 5% of the interspike intervals that fell outside of 3 SD from the mean of all interspike intervals in that cell. The analysis of PC firing was performed using Clampfit 10.2 (Molecular Devices). Data was plotted as the instantaneous firing rate every 100 ms for the entire recording duration. Once a bursting activity was established during the first 15-20 min of recordings, the bath solution was switched to the aCSF containing 50 uM CHZ, 10 µM 2o or 10 µM 2q for at least 20 min to determine the effect of the compound on the firing pattern of that PC.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A compound according to Formula (Ia) or a pharmaceutically acceptable salt thereof:

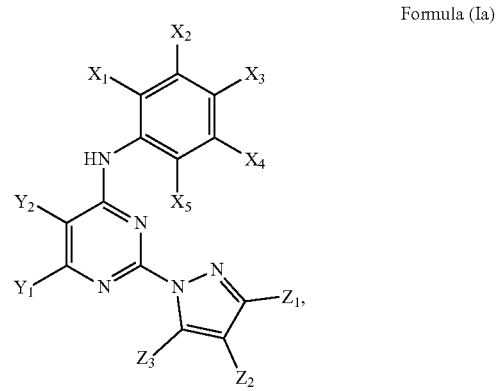

Formula (Ia)

wherein:
$X_1=X_2=X_4=X_5=H$, $X_3=SH$, $Y_1=CH_3$, $Y_2=H$, $Z_1=CH_3$, $Z_2=H$, and $Z_3=CH_3$;
$X_1=X_2=X_4=X_5=H$, $X_3=NO_2$, $Y_1=CH_3$, $Y_2=H$, $Z_1=CH_3$, $Z_2=H$, and $Z_3=CH_3$;
$X_1=X_2=F$, $X_3=X_4=X_5=H$, $Y_1=CH_3$, $Y_2=H$, $Z_1=CH_3$, $Z_2=H$, and $Z_3=CH_3$;
$X_1=X_4=F$, $X_2=X_3=X_5=H$, $Y_1=CH_3$, $Y_2=H$, $Z_1=CH_3$, $Z_2=H$, and $Z_3=CH_3$;

$X_1$=F, $X_2$=H, $X_3$=Cl, $X_4$=$X_5$=H, $Y_1$=$CH_3$, $Y_2$=H, $Z_1$=$CH_3$, $Z_2$=H, and $Z_3$=$CH_3$;

$X_1$=$X_4$=$X_5$=H, $X_2$=Cl, $X_3$=$CF_3$, $Y_1$=$CH_3$, $Y_2$=$CH_3$, $Z_1$=$CH_3$, $Z_2$=H, and $Z_3$=$CH_3$;

$X_1$=F, $X_2$=$X_3$=$X_5$=H, $X_4$=Cl, $Y_1$=$CH_3$, $Y_2$=H, $Z_1$=$CH_3$, $Z_2$=H, and $Z_3$=$CH_3$; or $X_1$=$X_4$=$X_5$=H, $X_2$=Cl, $X_3$=F, $Y_1$=$NH_2$, $Y_2$=H, $Z_1$=$CH_3$, $Z_2$=H, and $Z_3$=$CH_3$.

2. The compound of claim 1, wherein $X_1$=$X_2$=$X_4$=$X_5$=H, $X_3$=SH, $Y_1$=$CH_3$, $Y_2$=H, $Z_1$=$CH_3$, $Z_2$=H, and $Z_3$=$CH_3$.

3. The compound of claim 1, wherein $X_1$=$X_2$=$X_4$=$X_5$=H, $X_3$=$NO_2$, $Y_1$=$CH_3$, $Y_2$=H, $Z_1$=$CH_3$, $Z_2$=H, and $Z_3$=$CH_3$.

4. The compound of claim 1, wherein $X_1$=$X_2$=F, $X_3$=$X_4$=$X_5$=H, $Y_1$=$CH_3$, $Y_2$=H, $Z_1$=$CH_3$, $Z_2$=H, and $Z_3$=$CH_3$.

5. The compound of claim 1, wherein $X_1$=$X_4$=F, $X_2$=$X_3$=$X_5$=H, $Y_1$=$CH_3$, $Y_2$=H, $Z_1$=$CH_3$, $Z_2$=H, and $Z_3$=$CH_3$.

6. The compound of claim 1, wherein $X_1$=F, $X_2$=H, $X_3$=Cl, $X_4$=$X_5$=H, $Y_1$=$CH_3$, $Y_2$=H, $Z_1$=$CH_3$, $Z_2$=H, and $Z_3$=$CH_3$.

7. The compound of claim 1, wherein $X_1$=F, $X_2$=$X_3$=$X_5$=H, $X_4$=Cl, $Y_1$=$CH_3$, $Y_2$=H, $Z_1$=$CH_3$, $Z_2$=H, and $Z_3$=$CH_3$.

8. The compound of claim 1, wherein $X_1$=$X_4$=$X_5$=H, $X_2$=Cl, $X_3$=$CF_3$, $Y_1$=$CH_3$, $Y_2$=$CH_3$, $Z_1$=$CH_3$, $Z_2$=H, $Z_3$=$CH_3$.

9. The compound of claim 1, wherein $X_1$=$X_4$=$X_5$=H, $X_2$=Cl, $X_3$=F, $Y_1$=$NH_2$, $Y_2$=H, $Z_1$=$CH_3$, $Z_2$=H, and $Z_3$=$CH_3$.

\* \* \* \* \*